US010004518B2

(12) United States Patent
Fallin et al.

(10) Patent No.: US 10,004,518 B2
(45) Date of Patent: *Jun. 26, 2018

(54) SOFT TISSUE RECONSTRUCTION

(71) Applicant: Smith & Nephew, Inc., Memphis, TN (US)

(72) Inventors: T. Wade Fallin, Hyde Park, UT (US); M. Mary Sinnott, Logan, UT (US); Patrick Michel White, West Chester, PA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/471,013

(22) Filed: Mar. 28, 2017

(65) Prior Publication Data

US 2017/0196574 A1   Jul. 13, 2017

Related U.S. Application Data

(63) Continuation of application No. 15/066,863, filed on Jan. 26, 2016, now Pat. No. 9,603,612, which is a continuation of application No. 13/654,013, filed on Oct. 17, 2012, now Pat. No. 9,241,784, which is a continuation-in-part of application No. 13/527,648, filed on Jun. 20, 2012, now Pat. No. 8,784,427.

(60) Provisional application No. 61/506,000, filed on Jul. 8, 2011, provisional application No. 61/568,137, filed on Dec. 7, 2011, provisional application No. 61/505,992, filed on Jul. 8, 2011, provisional application No. 61/506,004, filed on Jul. 8, 2011.

(51) Int. Cl.
*A61B 17/17* (2006.01)
*A61F 2/08* (2006.01)

(52) U.S. Cl.
CPC ...... *A61B 17/1714* (2013.01); *A61B 17/1739* (2013.01); *A61B 17/1775* (2016.11); *A61F 2/0805* (2013.01); *A61F 2/08* (2013.01)

(58) Field of Classification Search
CPC .................................................. A61F 2/0805
See application file for complete search history.

(56) References Cited

U.S. PATENT DOCUMENTS

| 2,301,500 | A | 11/1942 | Anderson |
| 2,697,433 | A | 12/1954 | Zehnder |
| 4,686,972 | A | 8/1987 | Kurland |
| 4,739,751 | A | 4/1988 | Sapega et al. |
| 4,781,182 | A | 11/1988 | Purnell et al. |

(Continued)

FOREIGN PATENT DOCUMENTS

| GB | 2475491 A | 5/2011 |
| WO | 2008043380 A1 | 4/2008 |
| WO | 2008076559 A1 | 6/2008 |

OTHER PUBLICATIONS

Australian Patent Examination Report; Australian Patent Office; Australian Patent Application No. 2012282919; dated Apr. 14, 2016; 3 pages.

(Continued)

*Primary Examiner* — Andrew Yang
(74) *Attorney, Agent, or Firm* — Taft Stettinius & Hollister LLP

(57) ABSTRACT

Methods and instruments for reconstructing soft tissues of a skeletal joint such as for example of the foot or hand are presented.

20 Claims, 28 Drawing Sheets

(56) References Cited

U.S. PATENT DOCUMENTS

| | | | |
|---|---|---|---|
| 4,823,780 | A | 4/1989 | Odensten et al. |
| 4,883,048 | A | 11/1989 | Purnell et al. |
| 4,929,247 | A | 5/1990 | Rayhack |
| 4,964,861 | A | 10/1990 | Agee et al. |
| 5,042,983 | A | 8/1991 | Rayhack |
| 5,059,201 | A | 10/1991 | Asnis |
| 5,112,335 | A | 5/1992 | Laboureau et al. |
| 5,112,337 | A | 5/1992 | Paulos et al. |
| 5,176,685 | A | 1/1993 | Rayhack |
| 5,520,693 | A | 5/1996 | McGuire et al. |
| 5,968,050 | A | 10/1999 | Torrie |
| 6,007,535 | A | 12/1999 | Rayhack et al. |
| 6,187,011 | B1 | 2/2001 | Torrie |
| 6,725,082 | B2 | 4/2004 | Satie et al. |
| 6,878,150 | B1 | 4/2005 | McGuire et al. |
| 7,025,770 | B2 | 4/2006 | McGuire et al. |
| 7,575,578 | B2 | 8/2009 | Wetzler et al. |
| 8,110,000 | B2 | 2/2012 | Collins |
| 8,277,459 | B2 * | 10/2012 | Sand .................. A61B 17/1682 606/86 R |
| 8,784,427 | B2 | 7/2014 | Fallin et al. |
| 8,951,263 | B2 | 2/2015 | Sinnott et al. |
| 2003/0078599 | A1 | 4/2003 | O'Quinn et al. |
| 2003/0078600 | A1 | 4/2003 | O'Quinn et al. |
| 2003/0216742 | A1 | 11/2003 | Wetzler et al. |
| 2004/0015177 | A1 | 1/2004 | Chu |
| 2007/0088362 | A1 | 4/2007 | Bonutti et al. |
| 2007/0233128 | A1 | 10/2007 | Schmieding et al. |
| 2009/0171355 | A1 * | 7/2009 | Amis .................. A61B 17/1714 606/53 |
| 2009/0254126 | A1 | 10/2009 | Orbay et al. |
| 2010/0057216 | A1 | 3/2010 | Gannoe et al. |
| 2010/0324563 | A1 | 12/2010 | Green, II et al. |
| 2011/0066165 | A1 | 3/2011 | Skinlo et al. |
| 2011/0144647 | A1 | 6/2011 | Appenzeller et al. |
| 2011/0208198 | A1 | 8/2011 | Anderson et al. |
| 2013/0041466 | A1 | 2/2013 | Fallin et al. |

OTHER PUBLICATIONS

Blitz et al.; "Plantar Plate Repair of the Second Metatarsophalangeal Joint: Technique and Tips"; Journal of Foot Ankle Surgery; 2004; 43(4):266-270.

Couthlin et al.; "Second MTP Joint Instability; Grading of the Deformity and Description of Surgical Repair of Capsular Insufficiency"; The Physician and Sportmedicine; Sep. 3, 2011; 39(3):132-141.

Fleming and Camasta; "Plantar Plate Dysfunction"; Chapter 4; 2002; pp. 22-28; http://www.podiatryinstitute.com/pdfs/Update_2002/2002_04.pdf.

Gregg et al.; "Plantar Plate Repair and Well Osteotomy for Metatarsophalangeal Joint Instability"; Foot & Ankle Surgery; 2007; 13:116-121.

Nery et al.; "Lesser Metatarsophalangeal Joint Instability: Prospective Evaluation and Repair of Plantar Plate and Capsular Insufficiency"; Foot & Ankle International; Apr. 2012; vol. 33(4):301-311.

Well et al. "Anatomic Plantar Plate Repair Using the Well Matatarsal Osteotomy Approach"; Foot and Ankle Specialist; Jun. 22, 2011, 4:145-150. Originally published online on Mar. 18, 2011, http://fas.sagepub.com/content/4/4/145.

Extended European Search Report; European Patent Office; European Application No. 12810809.9; dated Feb. 15, 2016; 21 pages.

* cited by examiner

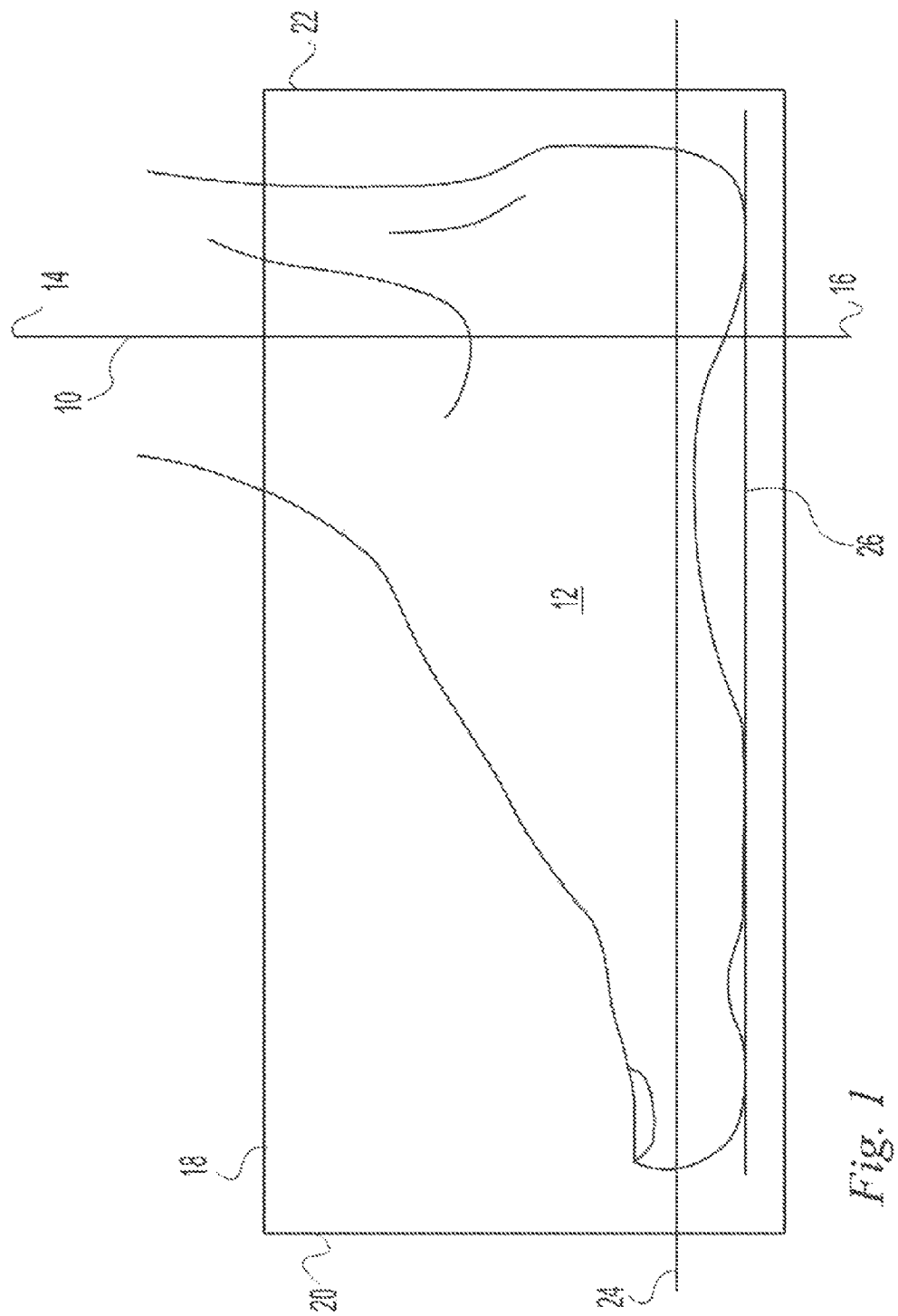

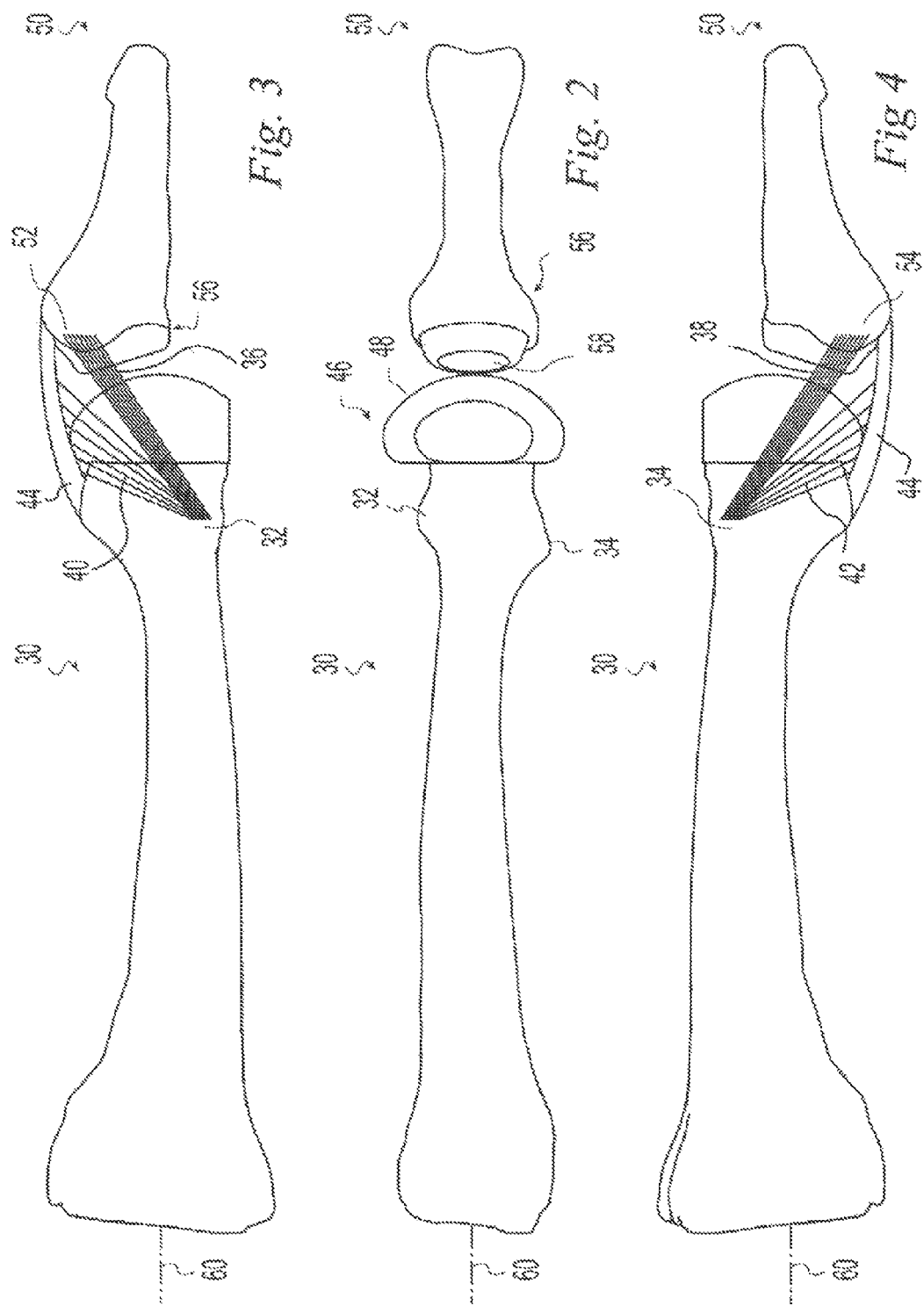

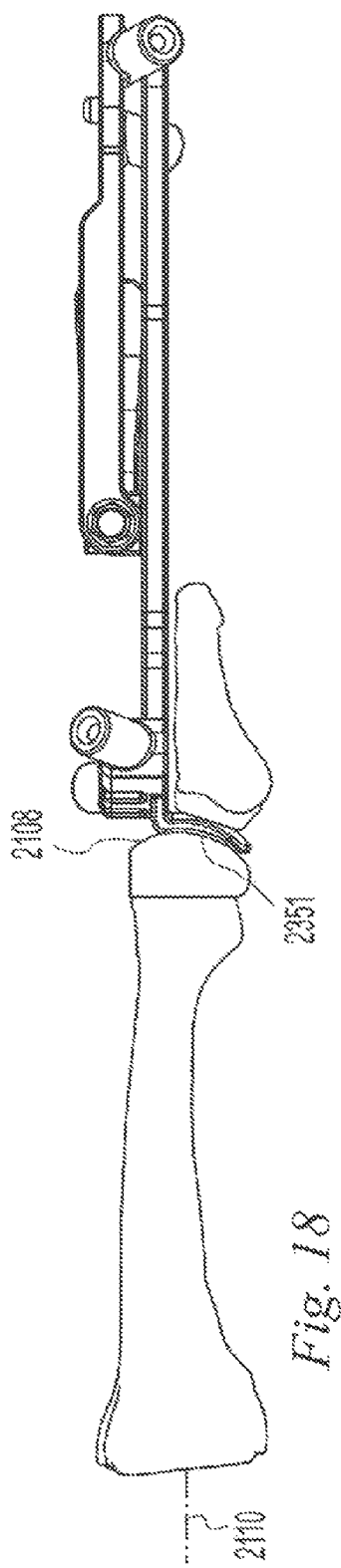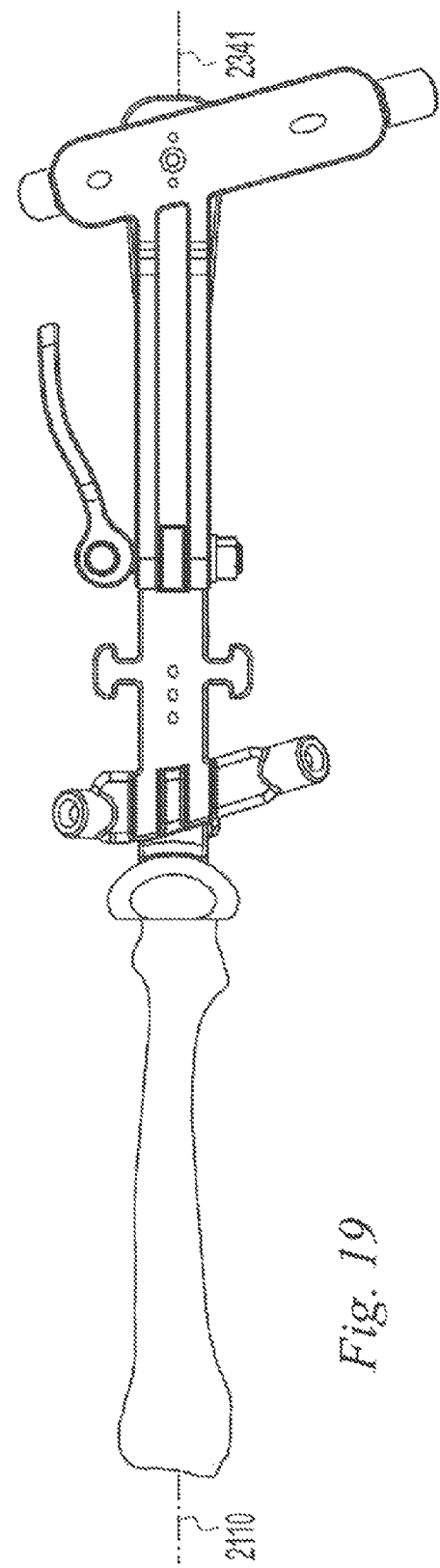

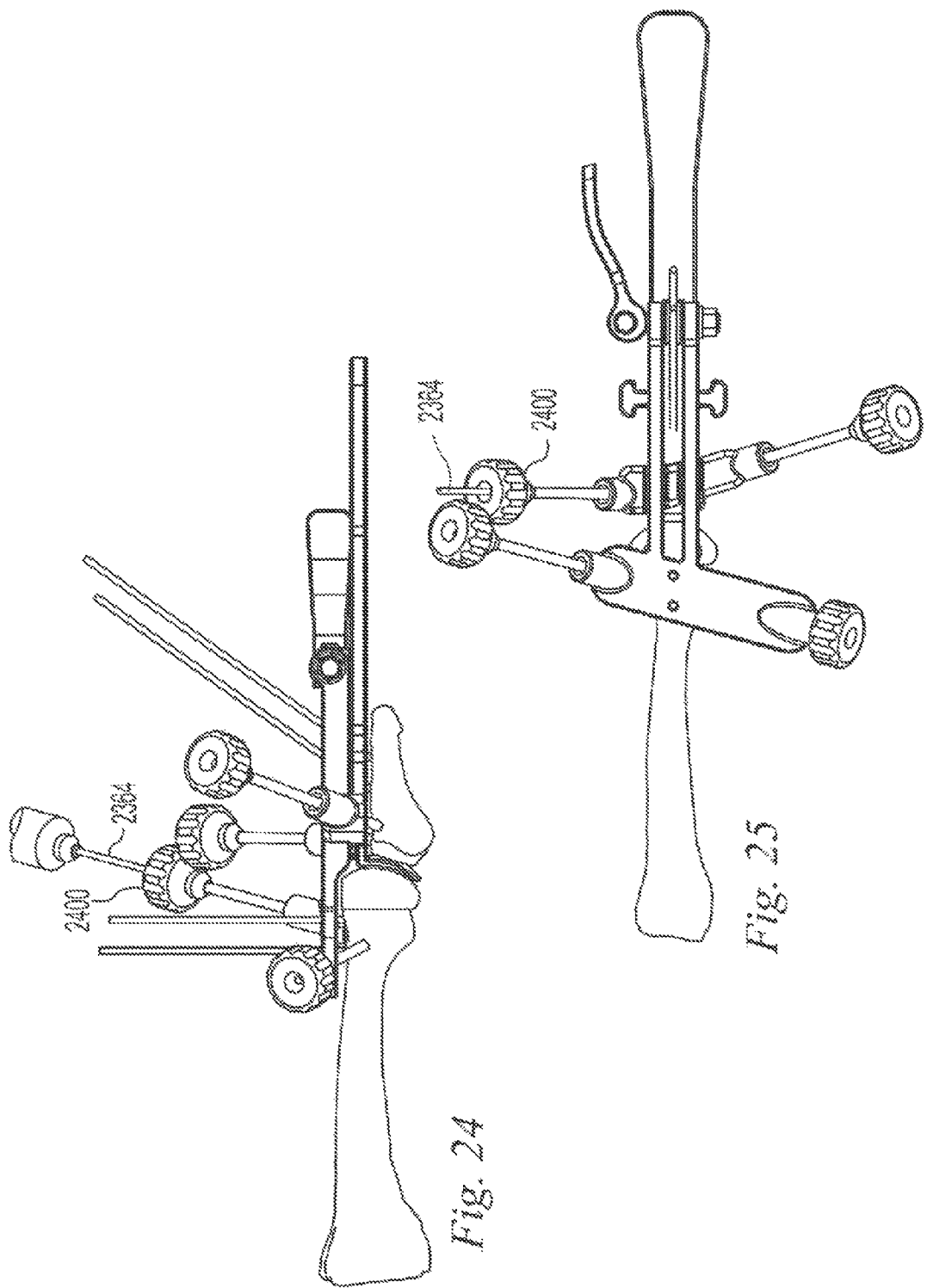

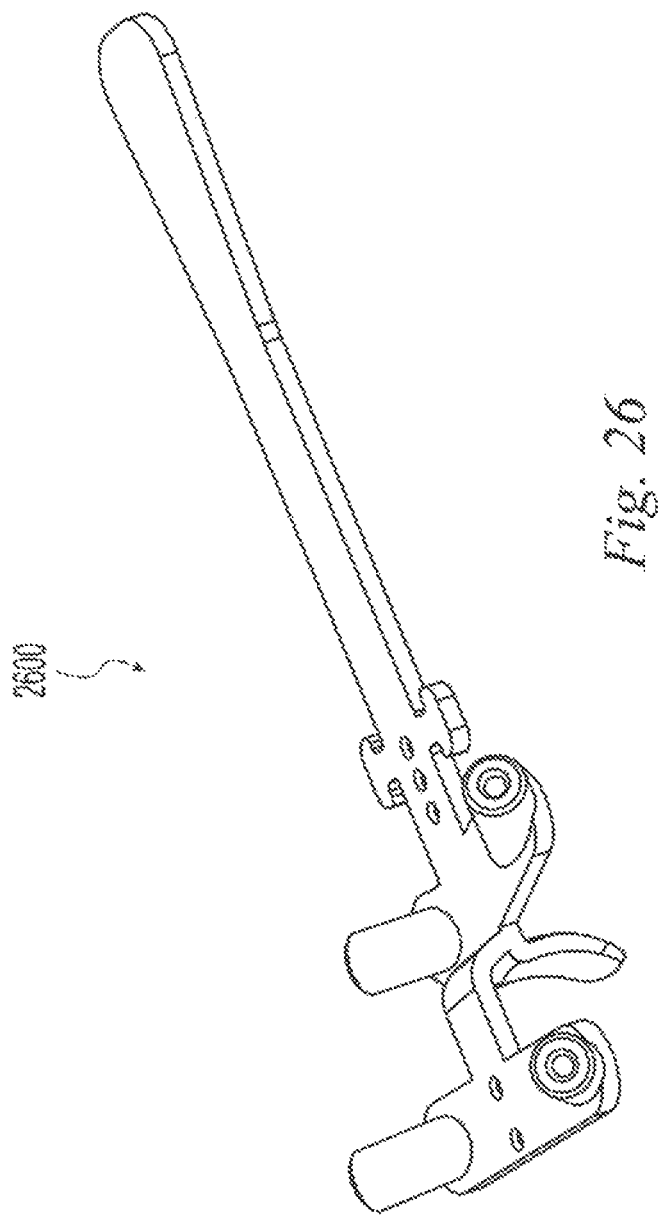

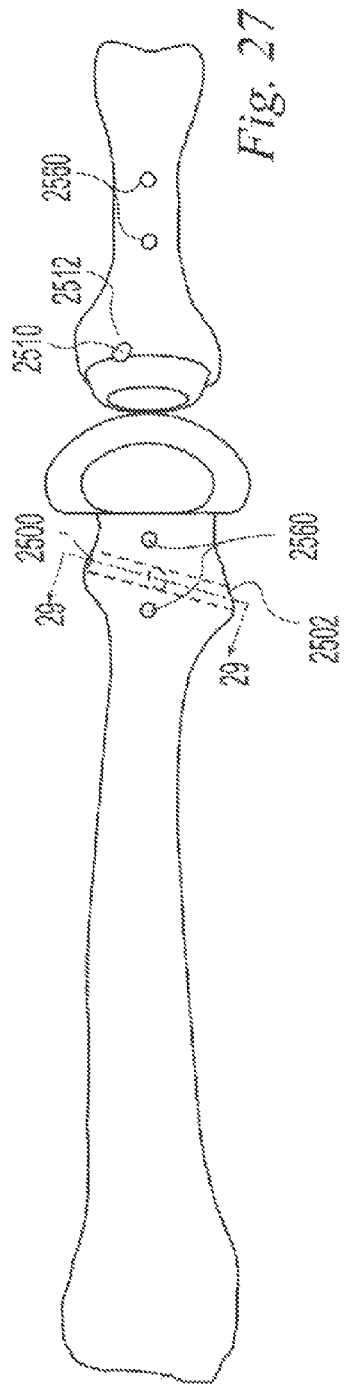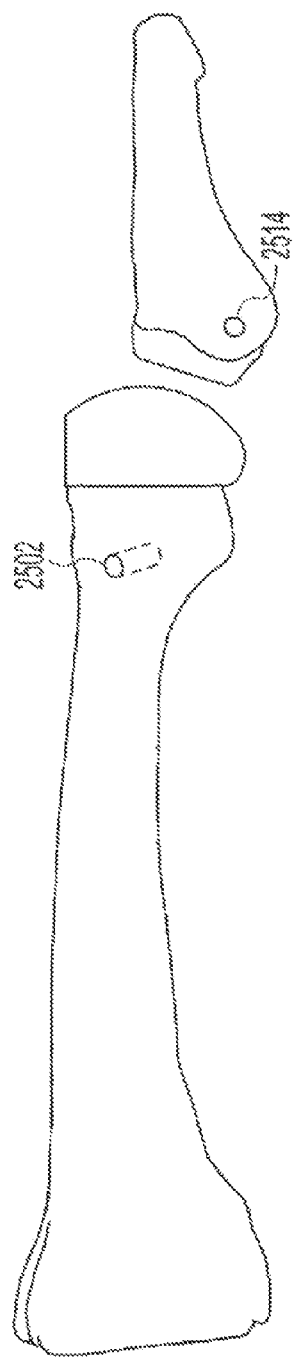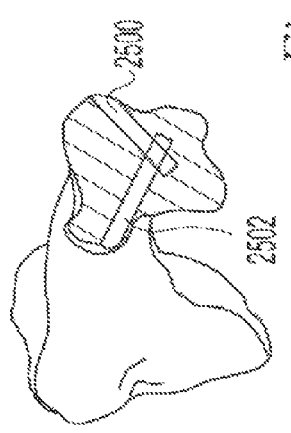

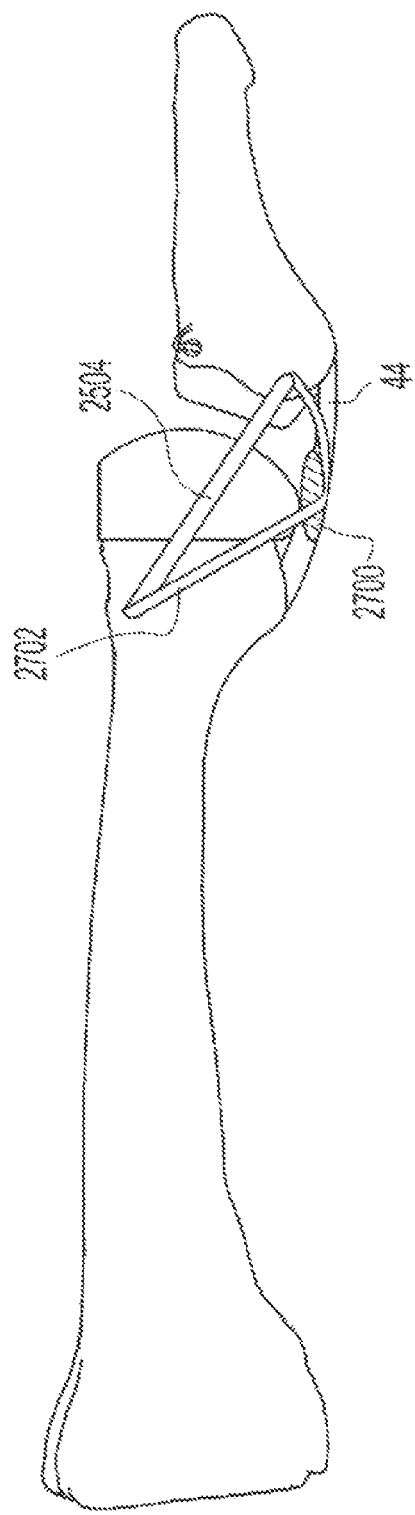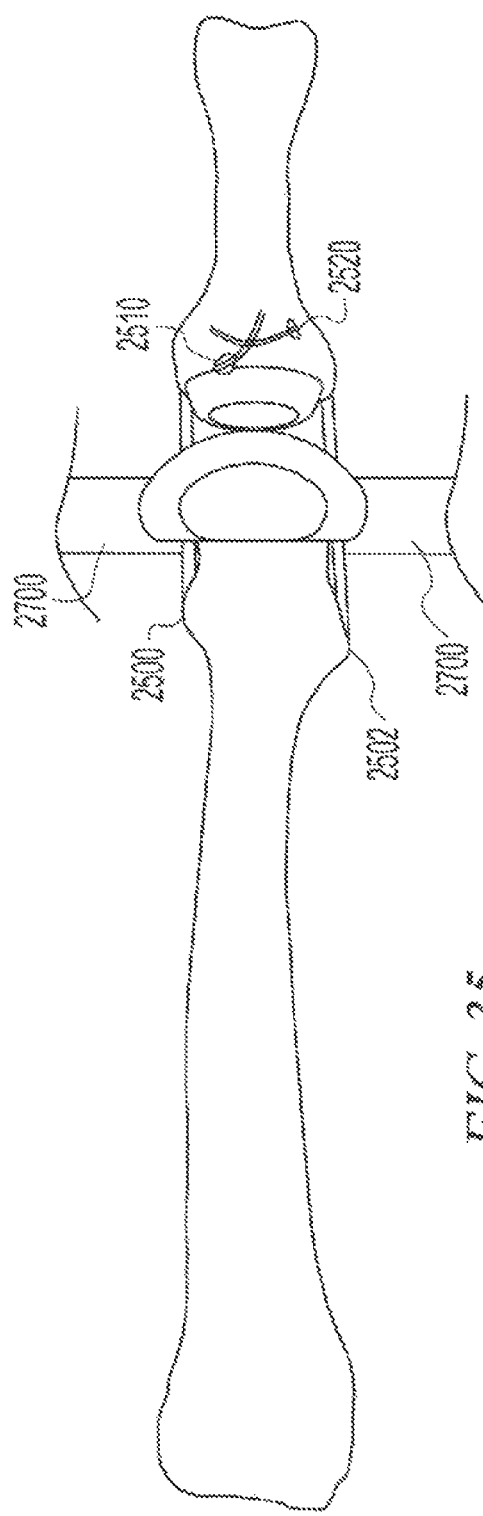
FIG. 34
FIG. 35

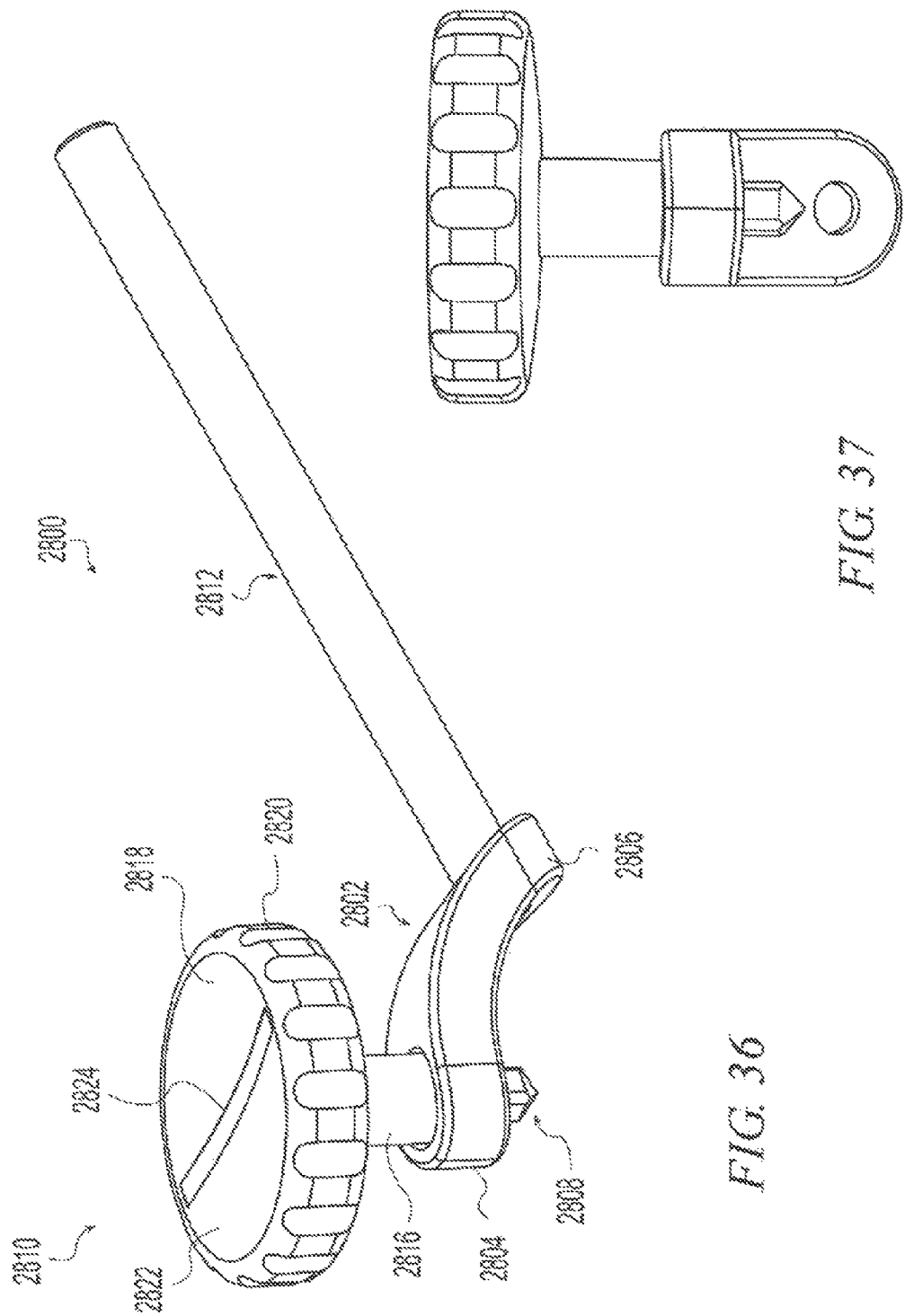

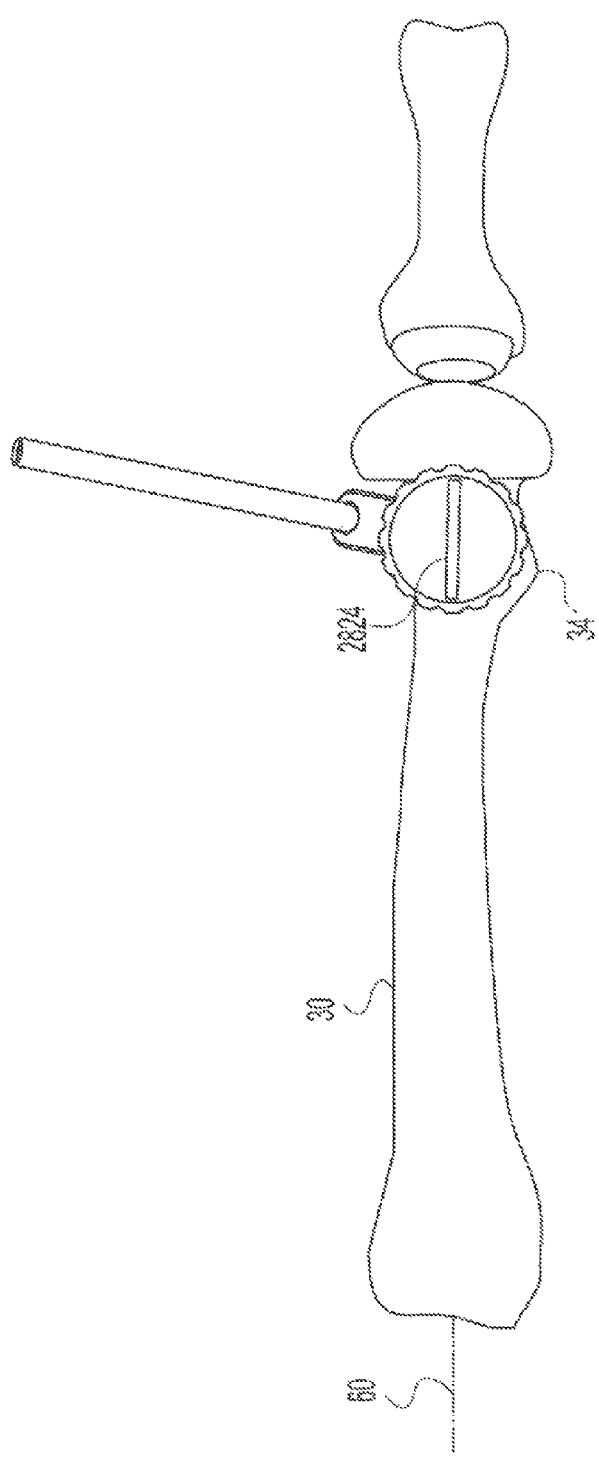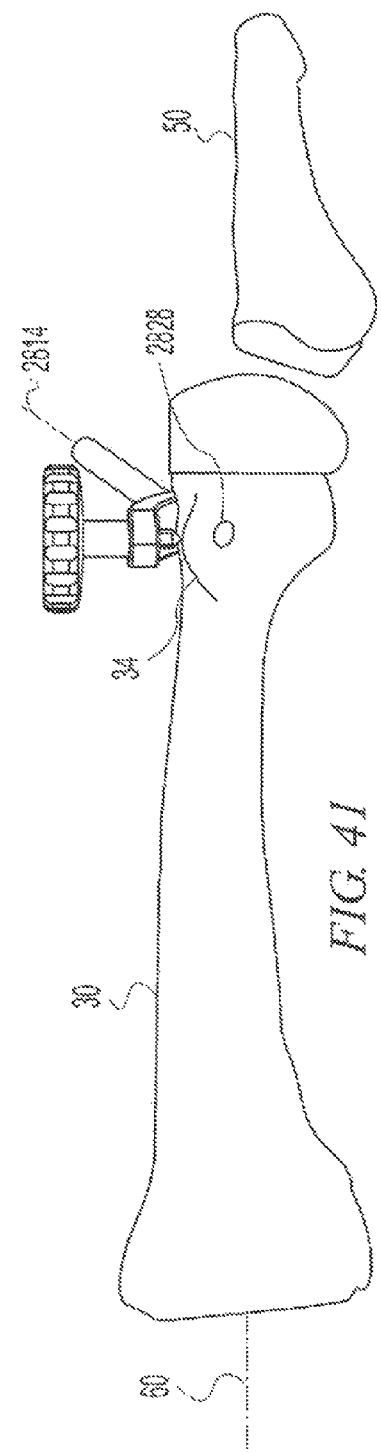
FIG. 40
FIG. 41

US 10,004,518 B2

SOFT TISSUE RECONSTRUCTION

CROSS-REFERENCE TO RELATED APPLICATIONS

This application is a continuation application of U.S. patent application Ser. No. 15/006,863, filed Jan. 26, 2016, which is a continuation application of U.S. patent application Ser. No. 13/654,013, filed Oct. 17, 2012 and issued as U.S. Pat. No. 9,241,784, which is a continuation-in-part of U.S. patent application Ser. No. 13/527,648, filed Jun. 20, 2012 and issued as U.S. Pat. No. 8,784,427, which claims the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, and U.S. Provisional Application No. 61/506,004, filed Jul. 8, 2011. All of the cross-referenced non-provisional and provisional applications are incorporated herein by reference in their entirety.

FIELD OF THE INVENTION

The invention relates to methods and instruments for reconstructing soft tissues of a skeletal joint such as for example of the foot or hand.

BACKGROUND

Various conditions may affect skeletal joints such as the elongation, shortening, or rupture of soft tissues associated with the joint. Joint function may be restored by reconstruction of the soft tissues associated with the joint.

SUMMARY

The present invention provides methods for reconstructing soft tissues associated with joints.

In one aspect of the invention, a method of reconstructing soft tissue adjacent a metapodial phalangeal joint of a human extremity includes forming a metapodial bone tunnel in the metapodial bone; forming a phalangeal bone tunnel in the proximal phalanx; placing a graft between the metapodial and phalangeal bone tunnels; and securing the graft.

In another aspect of the invention, a method of reconstructing soft tissue adjacent a metapodial phalangeal joint includes positioning a drill guide adjacent the joint; engaging a first reference portion of the drill guide with a first anatomic landmark; aligning a first guiding portion of the drill guide in alignment with a medial-dorsal aspect of the metapodial bone; aligning a second guiding portion of the drill guide in alignment with a lateral-dorsal aspect of the metapodial bone; guiding a cutter with the first guiding portion to form a first tunnel into the metapodial bone; and guiding a cutter with the second guiding portion to form a second tunnel into the metapodial bone intersecting the first tunnel.

In another aspect of the invention, a method of reconstructing soft tissue adjacent a metapodial phalangeal joint includes positioning a drill guide adjacent the joint; engaging a first reference portion of the drill guide with a first anatomic landmark; aligning a guiding portion of the drill guide in alignment with the proximal phalanx; and guiding a cutter with the guiding portion to form the phalangeal tunnel.

In another aspect of the invention, a method of reconstructing an accessory collateral ligament adjacent a metatarsophalangeal joint of a human foot includes positioning a drill guide adjacent the joint; aligning a first guiding portion of the drill guide in alignment with the anatomic attachment of an accessory collateral ligament on the metatarsus; aligning a second guiding portion of the drill guide in alignment with the proximal phalanx; guiding a cutter with the first guiding portion to form tunnel in the metatarsus; guiding a cutter with the second guiding portion to form a tunnel in the proximal phalanx; placing graft material at least partially into the first tunnel; placing graft material at least partially into the phalangeal tunnel; and securing the graft material in the tunnels.

In another aspect of the invention, a method of reconstructing an accessory collateral ligament adjacent a metatarsophalangeal joint of a human foot includes positioning a drill guide adjacent the joint; aligning a guiding portion of the drill guide in alignment with the anatomic attachment of an accessory collateral ligament on the metatarsus; guiding a cutter with the guiding portion to form a tunnel in the metatarsus; placing graft material such that it passes from the tunnel around a portion of the intermetatarsal ligament and back to the tunnel; and securing the graft material relative to the tunnel.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 1 is side elevation view of the human foot illustrating anatomic reference planes;

FIG. 2 is a dorsal view of the metatarsus and proximal phalanx of the right second metatarsophalangeal joint of the human foot;

FIG. 3 is a medial view of the bones of FIG. 2;

FIG. 4 is a lateral view of the bones of FIG. 2;

FIG. 18 is a side elevation view of the guide of FIG. 5 in use with an MTP joint;

FIG. 19 is a top plan view of the guide of FIG. 5 in use with an MTP joint;

FIG. 24 is a side elevation view of the guide of FIG. 5 in use with an MTP joint;

FIG. 25 is a top plan view of the guide of FIG. 5 in use with an MTP joint;

FIG. 26 is a perspective view of an illustrative example of a guide according to the present invention.

FIGS. 27-35 illustrate soft tissue reconstruction of the MTP joint of the human foot using tunnels formed with a guide according to the present invention;

FIG. 36 is a perspective view of an illustrative example of a guide according to the present invention;

FIG. 37 is front elevation view of the guide of FIG. 36;

FIG. 40 is a top plan view of the guide of FIG. 36 in use with an MTP joint;

FIG. 41 is a side elevation view of the guide of FIG. 36 in use with an MTP joint;

DESCRIPTION OF THE ILLUSTRATIVE EXAMPLES

Figure 5:
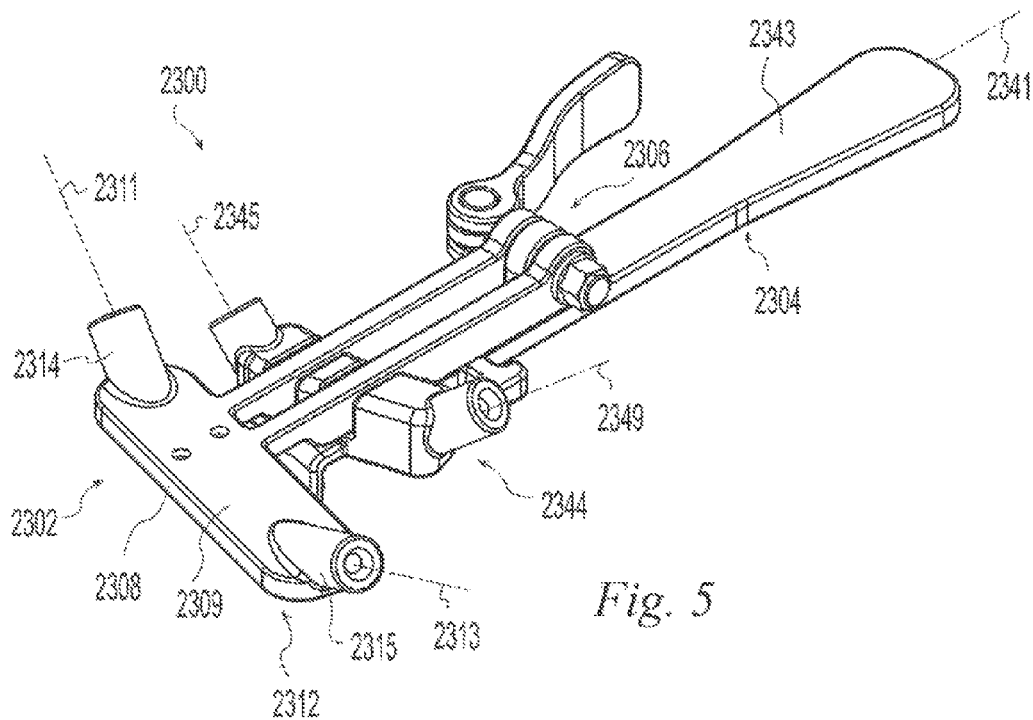
FIG. 5 is a perspective view of an illustrative example of a guide according to the present invention.
Figure 6:
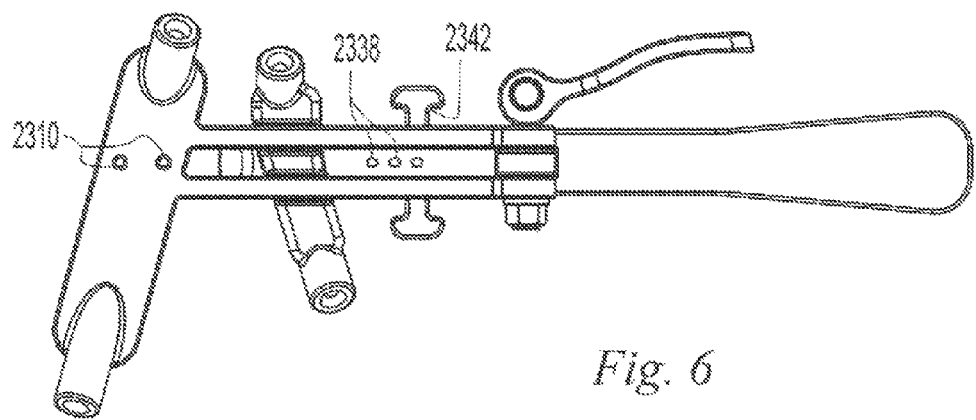
FIG. 6 is a top plan view of the guide of FIG. 5.
Figure 7:
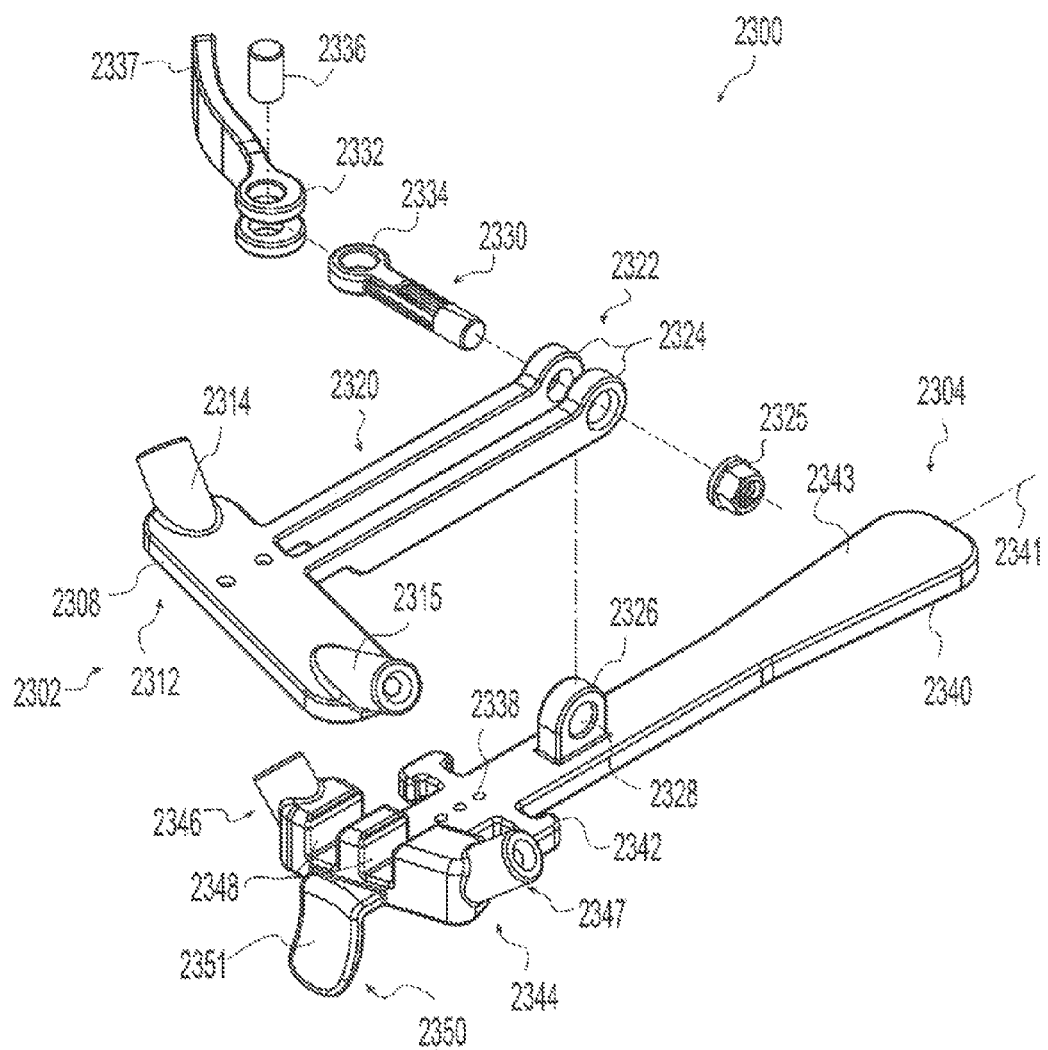
FIG. 7 is an exploded perspective view of the guide of FIG. 5.
Figure 8:
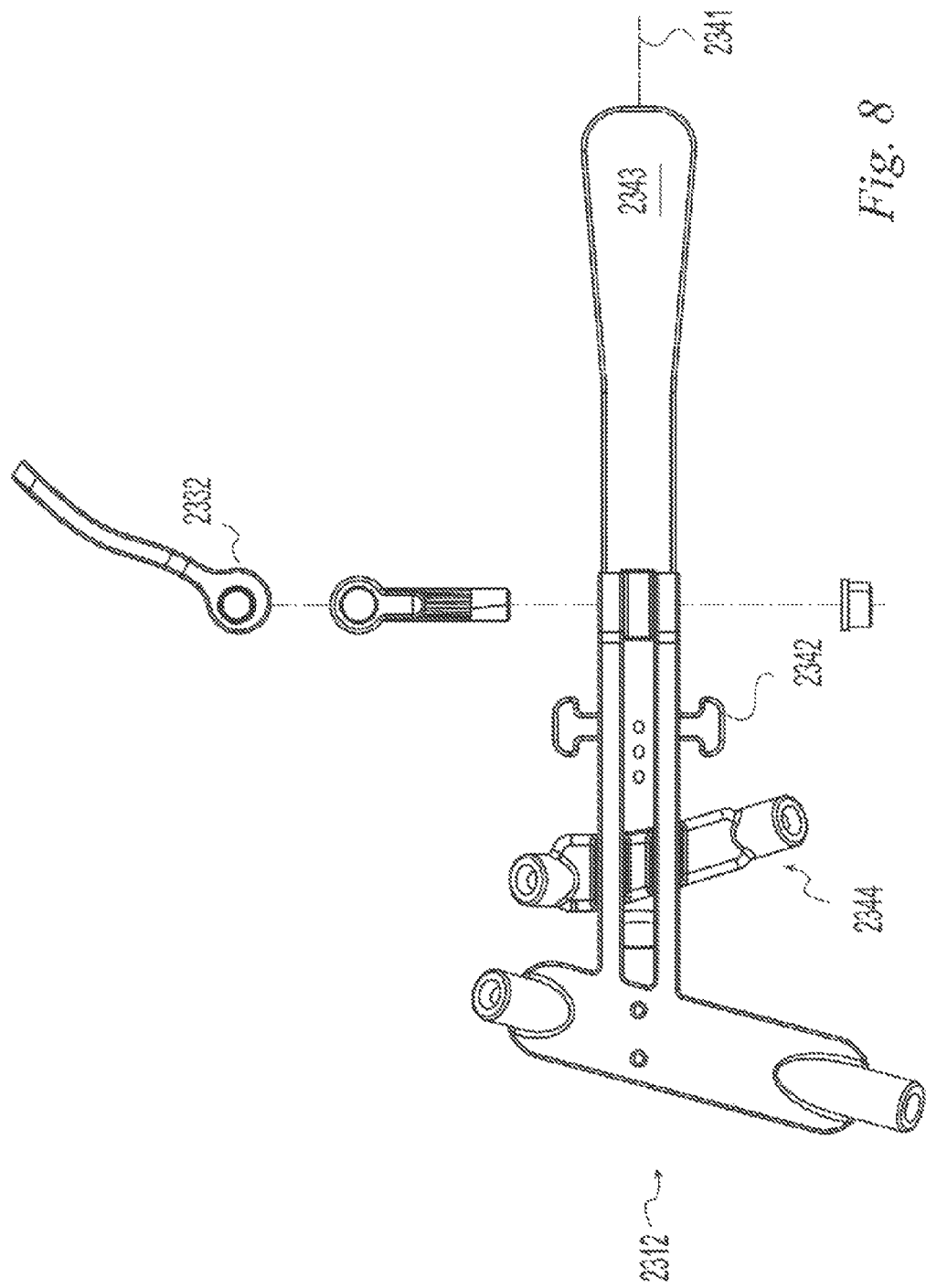
FIG. 8 is an exploded top plan view of the guide of FIG. 5.

The following illustrative examples illustrate instruments and techniques for treating skeletal joints. Instruments and techniques according to the present invention may be used in conjunction with any skeletal joint but the illustrative examples are shown in a size and form most suitable for the joints of the hand and foot. The hand and foot have a similar structure. Each has a volar aspect. In the hand the volar, or palmar, aspect includes the palm of the hand and is the gripping side of the hand. In the foot the volar, or plantar, aspect is the sole of the foot and is the ground contacting surface during normal walking. Both the hand and foot have a dorsal aspect opposite the volar aspect. Both the hand and foot include long bones referred to as metapodial bones. In the hand, the metapodial bones may also be referred to as metacarpal bones. In the foot, the metapodial bones may also be referred to as metatarsal bones. Both the hand and foot include a plurality of phalanges that are the bones of the digits, i.e. the fingers and toes. In both the hand and foot, each of the most proximal phalanges forms a joint with a corresponding metapodial bone. This joint includes a volar plate or band of connective tissue on the volar side of the joint. The joint also includes collateral ligaments on the medial and lateral sides of the joint. A transverse ligament, or intermetapodial ligament, connects the heads of the metapodial bones. In the hand the joint is typically referred to as the metacarpophalangeal joint having a palmar plate on the palmar side, collateral ligaments medially and laterally, and a transverse ligament connecting the metacarpals. In the foot the joint is typically referred to as the metatarsophalangeal joint having a plantar plate on the plantar side, collateral ligaments medially and laterally including proper collateral ligaments and accessory collateral ligaments, and a transverse ligament also known as the transverse metatarsal ligament or intermetatarsal ligament.

For convenience, the illustrative examples depict the use of instruments and techniques according to the present invention on metatarsophalangeal (MTP) joints of the human foot. The illustrative instruments and techniques are also suitable for use on metacarpophalangeal (MCP) joints of the human hand and other surgical sites. To better orient the reader, the MTP joint and basic anatomic references are explained in more detail below.

FIG. 1 illustrates the anatomic planes of the foot that are used for reference in this application. The coronal plane 10 extends from the medial aspect 12 to the lateral aspect of the foot and from dorsal 14 to plantar 16 and divides the foot between the toes and heel. The sagittal plane 18 extends anterior 20 to posterior 22 and dorsal 14 to plantar 16 and divides the foot into medial and lateral halves. The transverse plane extends anterior 20 to posterior 22 and medial to lateral parallel to the floor 26.

FIGS. 2-4 illustrate the metatarsus 30 and proximal phalanx 50 of the second MTP joint of the right foot. The medial and lateral epicondyles 32, 34, located on the medial-dorsal and lateral-dorsal aspects of the metatarsus 30 respectively, are the origins of the medial and lateral proper collateral ligaments (PCLs) 36, 38 and the medial and lateral accessory collateral ligaments (ACLs) 40, 42 of the MTP joint. The medial PCL inserts at the medial-plantar aspect 52 and the lateral PCL inserts at the lateral-plantar aspect 54 of the proximal phalanx 50. The medial and lateral ACLs fan out and insert into the medial and lateral borders of the plantar plate 44 respectively. The metatarsus includes a metatarsal head 46 having an articular surface 48 and the proximal phalanx includes a phalangeal head 56 having an articular surface 58. The metatarsus 30 further includes a longitudinal axis 60 extending length wise down the center of the bone.

The terms "suture" and "suture strand" are used herein to mean any strand or flexible member, natural or synthetic, able to be passed through material and useful in a surgical procedure including without limiting the above filaments, fabric, tendon, ligament, and fascia. The term "graft" is similarly defined as any member, natural or synthetic, that is used to reconstruct a soft tissue and includes sutures. The term "transverse" is used herein to mean crossing as in non-parallel. The term "bight" is used herein to mean a bend or loop formed in the intermediate portion of a suture.

FIGS. 5-13 illustrate an exemplary guide 2300 for guiding a cutter to cut a bone. In this illustrative example, the guide 2300 is configured as a drill guide to guide a drill, punch, pin, broach or the like to form holes in the bones adjacent the second MTP joint of the right human foot. The drill guide 2300 includes a pair of plate-like members 2302, 2304 joined at a hinge 2306 allowing a single degree of freedom such that the members may be pivoted between a first position and a second position. The members include a plurality of fixation holes for receiving fixation devices, e.g. fixation pins or screws, to secure the members to underlying bones and guide holes to guide the formation of tunnels in the underlying bones to facilitate soft tissue repair, replacement, and/or augmentation around the joint. The first member 2302 is configured to overlie the metatarsus and the second member 2304 is configured to overly the phalanx.

The first member 2302 includes a planar top surface 2309, a first end 2308 having fixation holes 2310, and a metatarsal guide portion 2312. The metatarsal guide portion 2312 has a feature for guiding a cutter. In the illustrative example of FIGS. 5-13, the metatarsal guide portion 2312 includes medial and lateral spaced apart, hollow, tabular extensions 2314, 2315 each projecting upwardly and outwardly from the top surface 2309 and configured as a drill guide able to guide a drill, punch, broach, pin or the like. The tubular extensions 2314, 2315 are oriented so that their axes 2311, 2313 intersect below the metatarsal guide portion 2312. A mounting yoke 2320 having opposed spaced apart arms extends from the first end 2308 to a second end 2322 defining a pair of eyelets 2324 which straddle a block 2326 mounted on the second member 2304. The block 2326 has a hole 2328 aligned with the eyelets 2324. A bolt 2330 and nut 2325 join the eyelets 2324 and block 2326. A locking cam 2332 is pinned to the head 2334 of the bolt 2330 for relative rotation about a pin 2336 and includes a lever 2337 extending from the cam for rotating the cam 2332 between a locked and unlocked position. The bolt 2330 and locking cam 2332 are operable to press the eyelets 2324 together against the block 2326 to frictionally lock the members 2302, 2304 in relative angular relationship.

The second member 2304 includes an elongated handle 2340 having a longitudinal axis 2341, a planar top surface 2343, fixation holes 2338 and a phalangeal guide portion 2344. The phalangeal guide portion 2344 has a feature for guiding a cutter. In the illustrative example of FIGS. 5-13, the phalangeal guide portion 2344 includes medial and lateral spaced apart, hollow, tubular extensions 2346, 2347 each projecting upwardly and configured as a drill guide able to guide a drill, punch, broach, pin or the like along axes 2345, 2349. The phalangeal guide portion 2344 includes a pair of grooves 2348 for receiving the yoke 2320 of the first member to increase the relative positional accuracy and stability of the members relative to one another when the members are locked in the second coaxial position. The second member 2304 further includes a head referencing member 2350 having a reference surface 2351 for engaging an anatomic landmark. In the illustrative example of FIGS. 5-13, the head referencing member 2350 has a concave spherical surface able to engage the articular surface of the metatarsal head. Opposite the concave surface is a convex back surface able to engage the articular surface of the phalangeal head. The second member further includes a pair of oppositely, laterally extending bosses 2342 for receiving a band to secure the guide 2300 to the phalanx.

Figure 9:
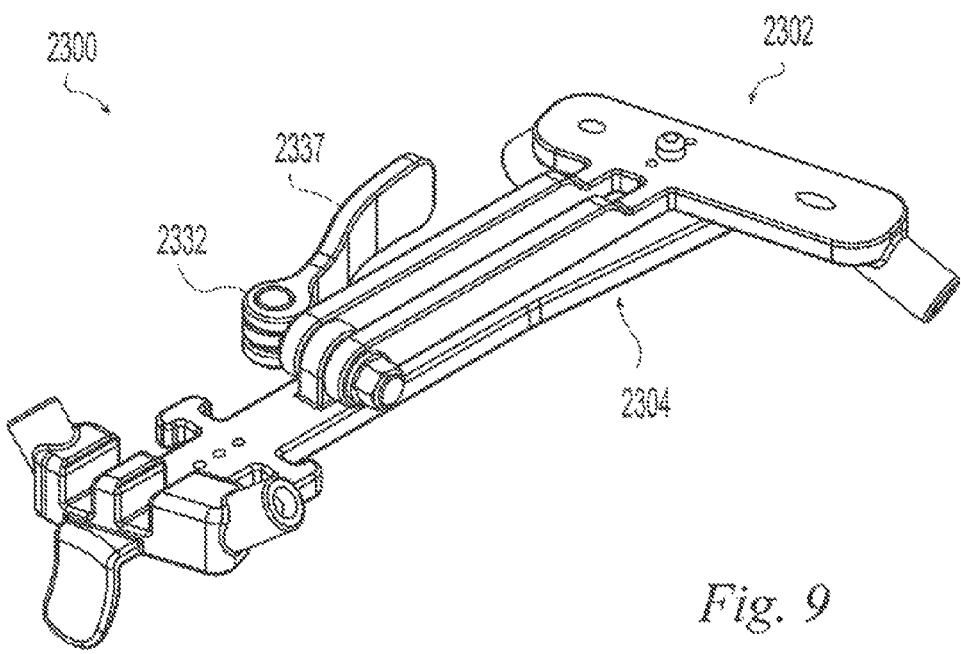
FIG. 9 is a perspective view of the guide of FIG. 5 showing a position of the guide.
Figure 10:
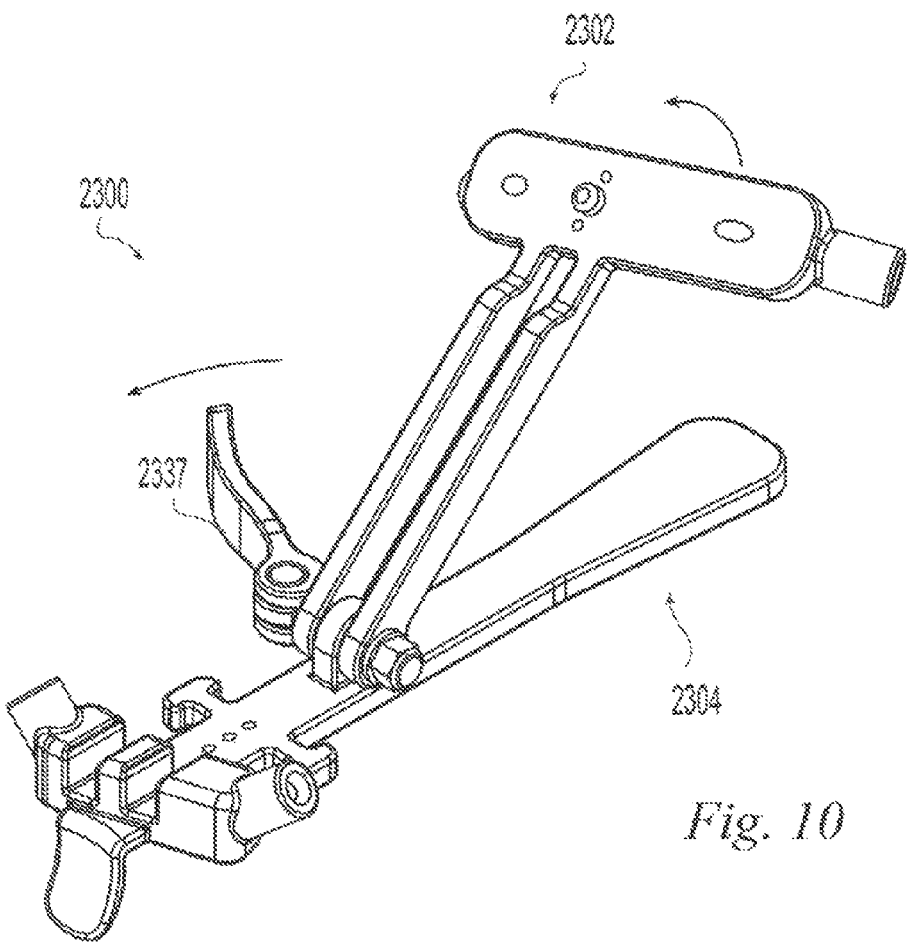
FIG. 10 is a perspective view of the guide of FIG. 5 showing a position of the guide.
Figure 11:
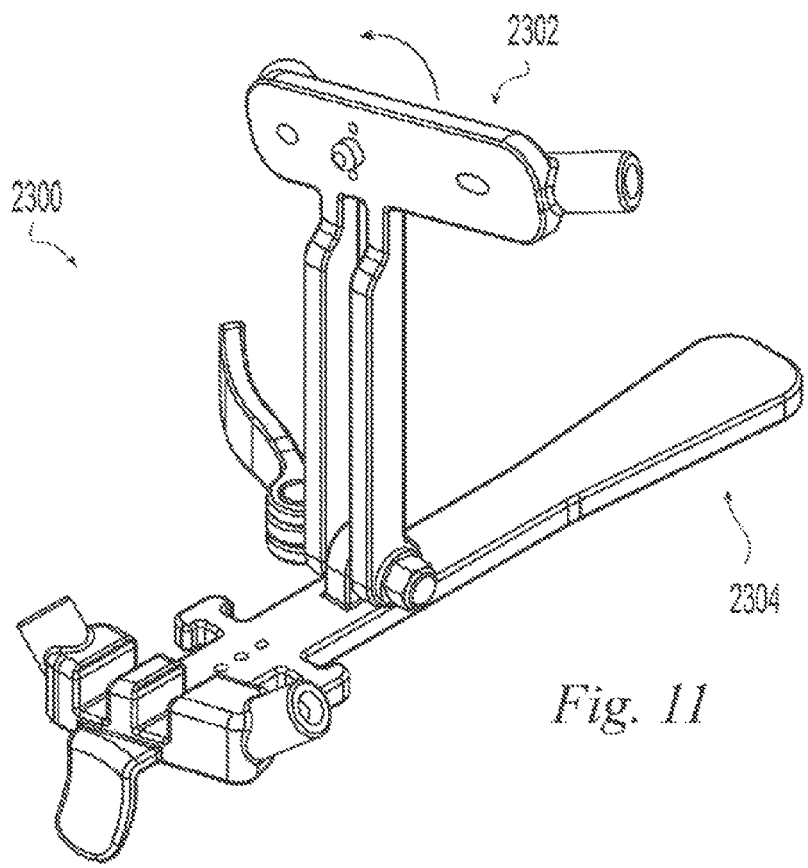
FIG. 11 is a perspective view of the guide of FIG. 5 showing a position of the guide.
Figure 12:
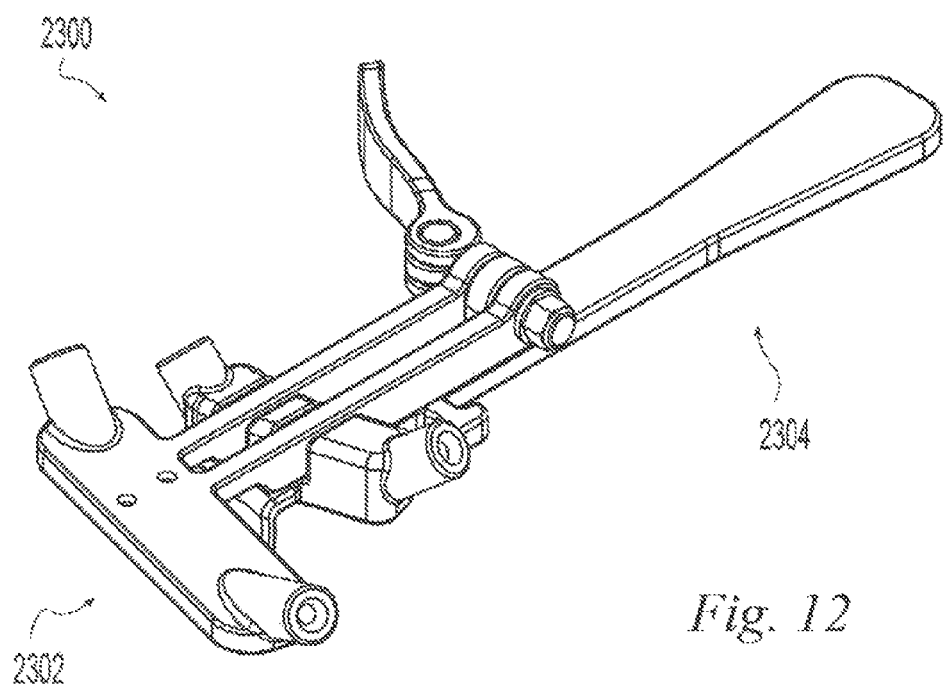
FIG. 12 is a perspective view of the guide of FIG. 5 showing a position of the guide.
Figure 13:
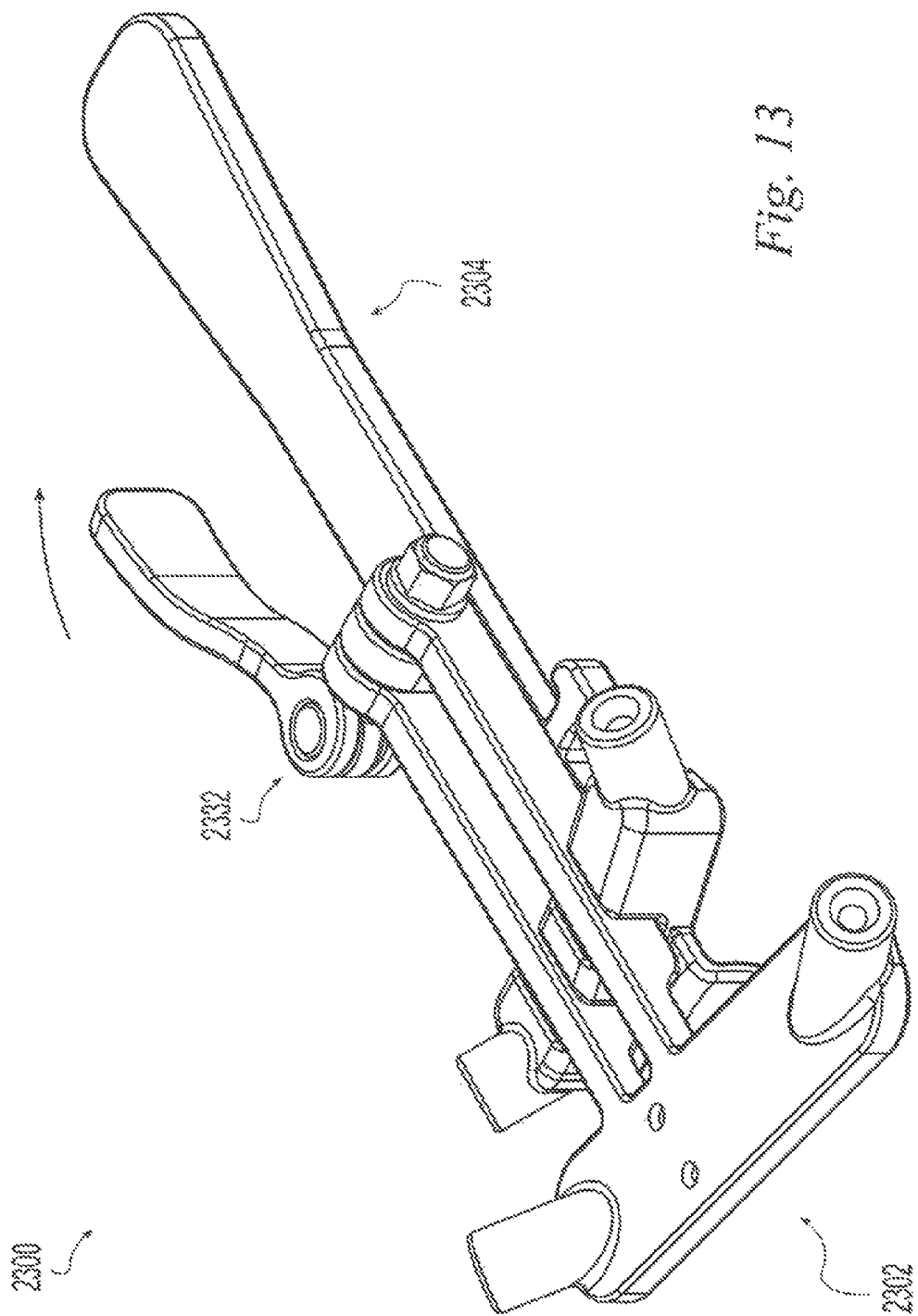
FIG. 13 is a perspective view of the guide of FIG. 5 showing a position of the guide.

FIG. 9 depicts the guide 2300 locked in the first parallel position. FIG. 10 depicts the guide 2300 with the cam 2332 unlocked by rotating lever 2337 and the first member 2302 rotated part-way toward the second position. FIG. 11 depicts the guide 2300 with the first member 2302 rotated further toward the second position. FIG. 12 depicts the guide 2300 with the first member rotated fully into the second position. FIG. 13 depicts the guide 2300 with the cam 2332 locked to fix the first and second members 2302, 2304 in the second position.

The relative position and orientation of the reference surface 2351 of the head referencing member 2350, the handle axis 2341, the handle top surface 2343, the phalangeal extensions 2346, 2347, and the metatarsal extension 2314, 2315 are determined from averaged anthropometric data relating the metatarsal head articular surface, metatarsal longitudinal axis, and transverse plane of the human body to the medial and lateral PCL origins and insertions when the guide 2300 is locked in the second position and placed on the bone with the reference surface 2350 engaged with the metatarsal head 2106, the handle axis 2341 parallel to the axis 110 of the metatarsus, and the handle top surface 2343 parallel to the transverse plane such that the metatarsal extension axes 2311, 2313 intersect the PCL origins and the phalangeal extension axes 2345, 2349 intersect the PCL origins.

Figure 14:
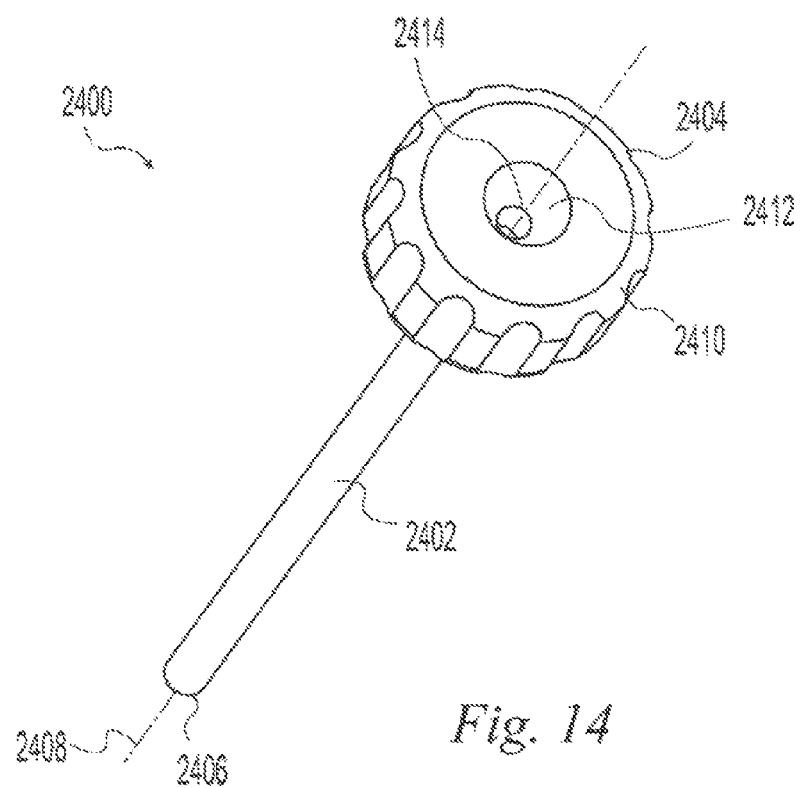
FIG. 14 is a perspective view of a tube useable with the guide of FIG. 5.
Figure 15:
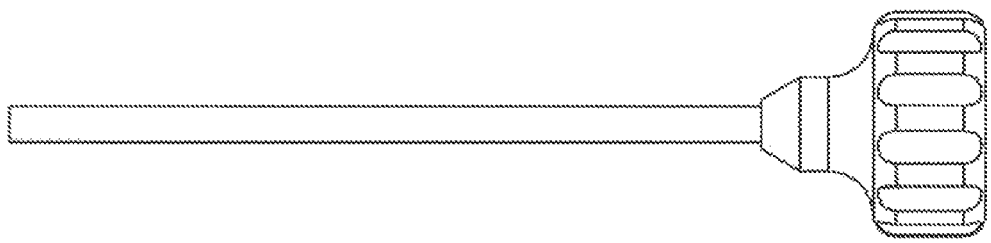
FIG. 15 is a side elevation view of the tube of FIG. 14.

FIGS. 14 and 15 illustrate an elongated tube 2400 that may be used with guide 2300 to protect soft tissue, facilitate engaging a cutter with the guide, and stabilize the cutter. For example, a long narrow drill, punch, pin, broach, or the like may be difficult to align with the extensions 2314, 2315, 2346, 2347 and/or may be so flexible that it tends to skive off the bone surface. The tube 2400 includes a tubular shaft 2402 having a proximal end 2404, a distal end 2406, and a longitudinal axis 2408 extending from the proximal end 2404 to the distal end 2406. The proximal end is radially enlarged to form a knob 2410. The knob 2410 includes a counter sink 2412 forming a funnel-like lead-in to the inner bore 2414 of the tubular shaft 2402. The outside of the shaft 2402 is sized to slide into the extensions of the guide 2300 and extend through the guide 2300 to contact the underlying bone. The shaft 2402 provides positive guidance of the cutter to the bone surface. The knob 2410 provides the user with a gripping surface spaced away from the inner bore 2414 to protect the user from being pricked by the cutter as the cutter is engaged with the inner bore 2414. The countersink 2412 guides the cutter into the inner bore 2414.

Figure 16:
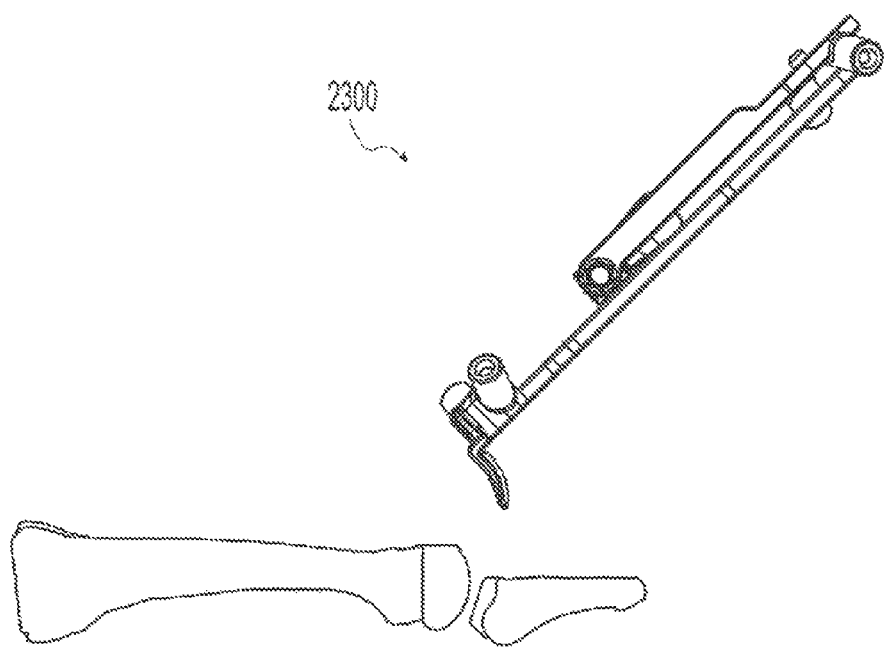
FIG. 16 is a side elevation view of the guide of FIG. 5 in use with an MTP joint.
Figure 17:
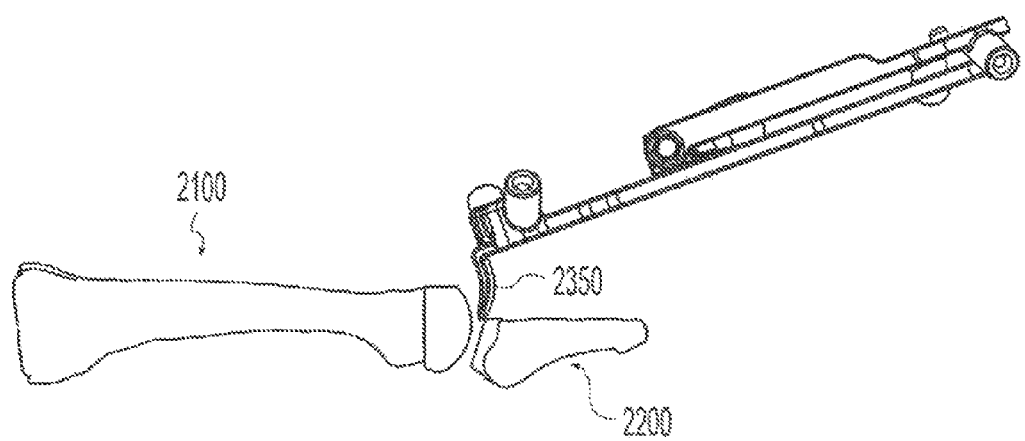
FIG. 17 is side elevation view of the guide of FIG. 5 in use with an MTP joint.
Figure 20:
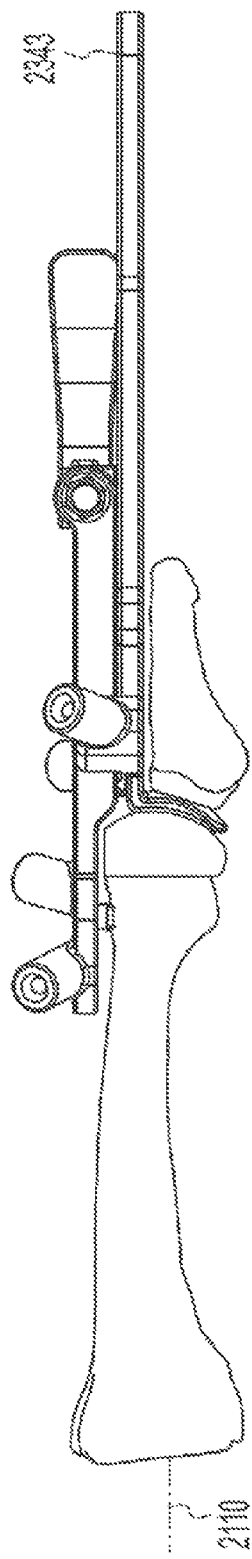
FIG. 20 is a side elevation view of the guide of FIG. 5 in use with an MTP joint.
Figure 21:
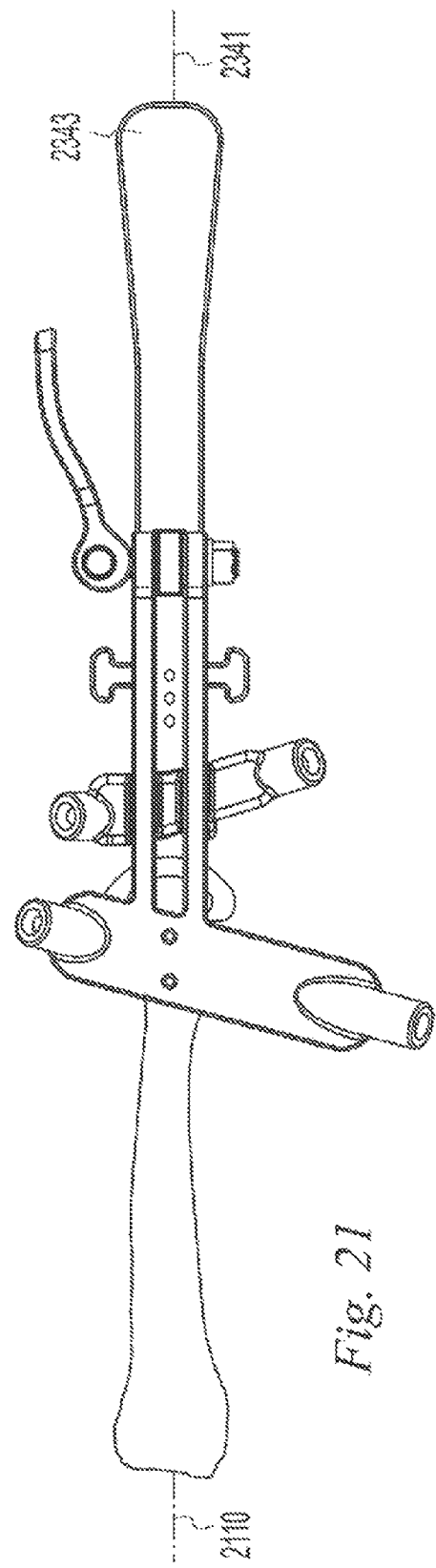
FIG. 21 is a top plan view of the guide of FIG. 5 in use with an MTP joint.
Figure 22:
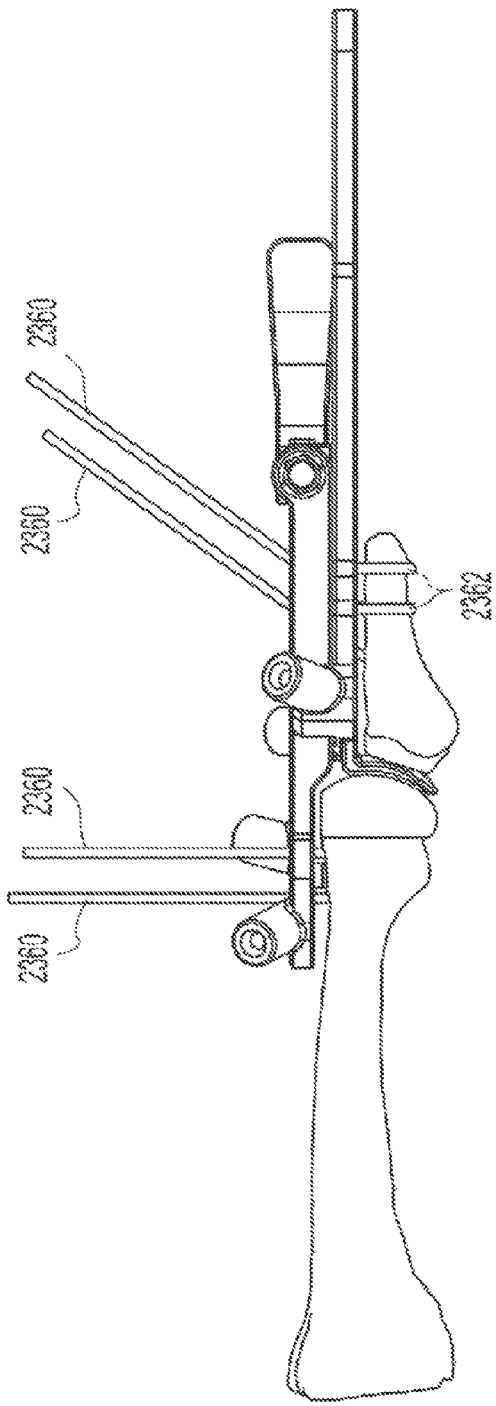
FIG. 22 is a side elevation view of the guide of FIG. 5 in use with an MTP joint.
Figure 23:
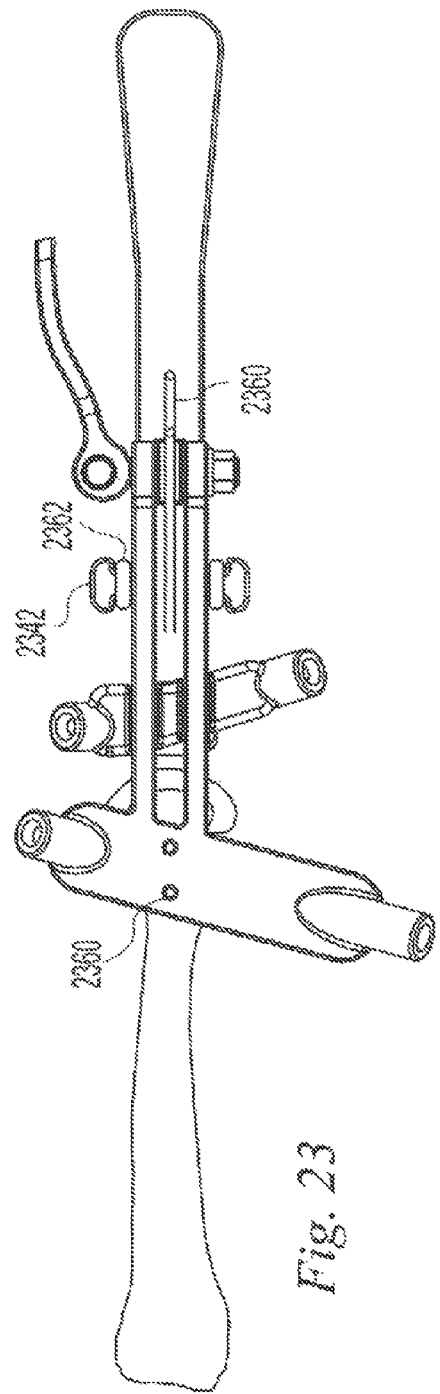
FIG. 23 is a top plan view of the guide of FIG. 5 in use with an MTP joint.

FIGS. 16-25 illustrate the guide 2300 in use to guide a cutter to form holes in the bones of the second MTP joint to facilitate, e.g., the reconstruction of the joint. The guide 2300 is brought near the joint with the first and second members folded in the first position as shown in FIG. 16. The head referencing member 2350 is inserted into the joint space between the metatarsus 2100 and phalanx 2200 as shown in FIG. 17. The concave reference surface 2351 is registered with the convex articular surface 2108 of the metatarsal head and the convex reference surface opposite the concave reference surface is registered with the concave articular surface of the proximal phalanx. The guide handle axis 2341 is oriented parallel to the axis 110 of the metatarsus and the guide handle top surface 2343 is oriented parallel to the transverse plane as shown in FIGS. 18 and 19. The first member is then pivoted into the second position as shown in FIGS. 20 and 21. The orientation of the guide 2300 may be checked again. The cam is actuated to lock the members relative to one another and fixation devices, e.g. pins 2360, may be placed in the guide fixation holes to fix the members to the bones as shown in FIGS. 22 and 23. An elastic band 2362 may be wrapped around the phalanx and engaged with the bosses 2342 to secure the second member 2304 to the phalanx in addition to, or as an alternative to, the fixation pins 2360.

Once the members are aligned and secured, the guide is used to guide a cutter to form one or more tunnels in the bones as shown in FIGS. 24 and 25. The cutter 2364 may be engaged directly with an extension of a guide portion and advanced into the bone. Alternatively, an elongated tube 2400 may first be engaged with the guide portion and extended to the bone surface. The cutter may then be engaged with the elongated tube 2400 and advanced into the bone.

The illustrative guide of FIGS. 5-13 includes two separate members hinged together. Alternatively, the guide may be provided as two separate guides each having a joint reference surface and useable independently to drill tunnels in the metatarsus and proximal phalanx. Alternatively, the hinge may be removed, and the two members combined into one non-movable unitary structure 2600 as shown in FIG. 26.

The illustrative guides of FIGS. 5 and 26 are configured to reference to the anatomy of the right second MTP joint of the human foot to guide a cutter to form tunnels in the metatarsus and phalanx that intersect the medial and lateral PCL origins and insertions to facilitate routing and attaching ligaments to reconstruct the PCLs. The guide may be mirrored for use on the left foot and the guide may be provided in sizes for different MTP joints and various sized feet. However, it has been found that the variation of the PCL origin and insertion anatomy is surprisingly small for the second MTP joint across a wide range of foot sizes and it is possible to provide a single sized guide for all left second MTP joints and another for all right MTP joints for feet from at least a woman's U.S. size 7 to a man's U.S. size 11.

FIGS. 27-35 illustrate soft tissue reconstruction of the MTP joint of the human foot using tunnels formed with the guides of FIG. 5 or 26. For example, a PCL or ACL may be partially or fully torn due to acute trauma or chronic progressive failure. Likewise, these soft tissues may be intentionally released from their bony origins or attachments to facilitate a surgical procedure. The instruments and techniques of the present invention provide a way to reconstruct these soft tissues.

FIGS. 27-31 depict an illustrative method to reconstruct a PCL. In the illustrative example of FIGS. 27-31, the medial PCL is reconstructed by placing a graft from the PCL origin on the distal aspect of the metatarsal to the PCL insertion on the proximal aspect of the proximal metatarsal. FIGS. 27-29 detail bone tunnels formed using guide 2300 or 2600. For example, the metatarsal guide portion 2312 has guided a cutter to form a medial-dorsal tunnel 2500 extending from the medial PCL origin into the metatarsus and a lateral-dorsal tunnel 2502 extending from the lateral PCL origin into the metatarsus. The tubular extensions 2314, 2315 of the metatarsal guide portion 2312 are oriented so that their axes intersect below the dorsal surface of the metatarsus. Thus, the tunnels 2500, 2502 intersect within the metatarsus and provide a path for fixing grafts to reconstruct one or both of the PCLs. The phalangeal guide portion 2344 has guided a cutter to form a tunnel 2510 extending from the medial-dorsal surface 2512 of the phalanx to the insertion 2514 of the lateral PCL on the lateral-plantar surface of the phalanx. The holes 2560 are formed by fixation members 2360 used to hold the guide in place.

Figure 30:
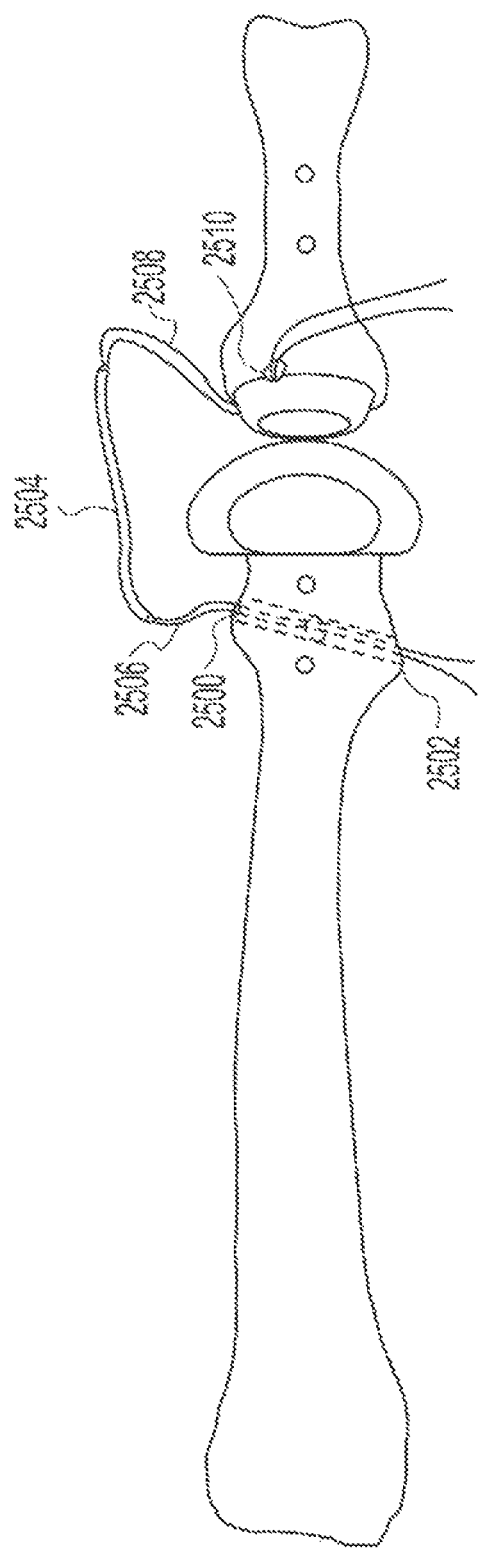

FIG. 30 depicts a graft 2504 with a proximal suture 2506 stitched to its proximal end and a distal suture 2508 stitched to its distal end. The proximal suture 2506 is threaded through the metatarsal bone tunnels by inserting it into the medial-dorsal tunnel 2500 and retrieving it from the lateral-dorsal tunnel 2502. The distal suture 2508 is threaded through the phalangeal bone tunnel 2510 by passing it from plantar to dorsal through the tunnel.

Figure 31:
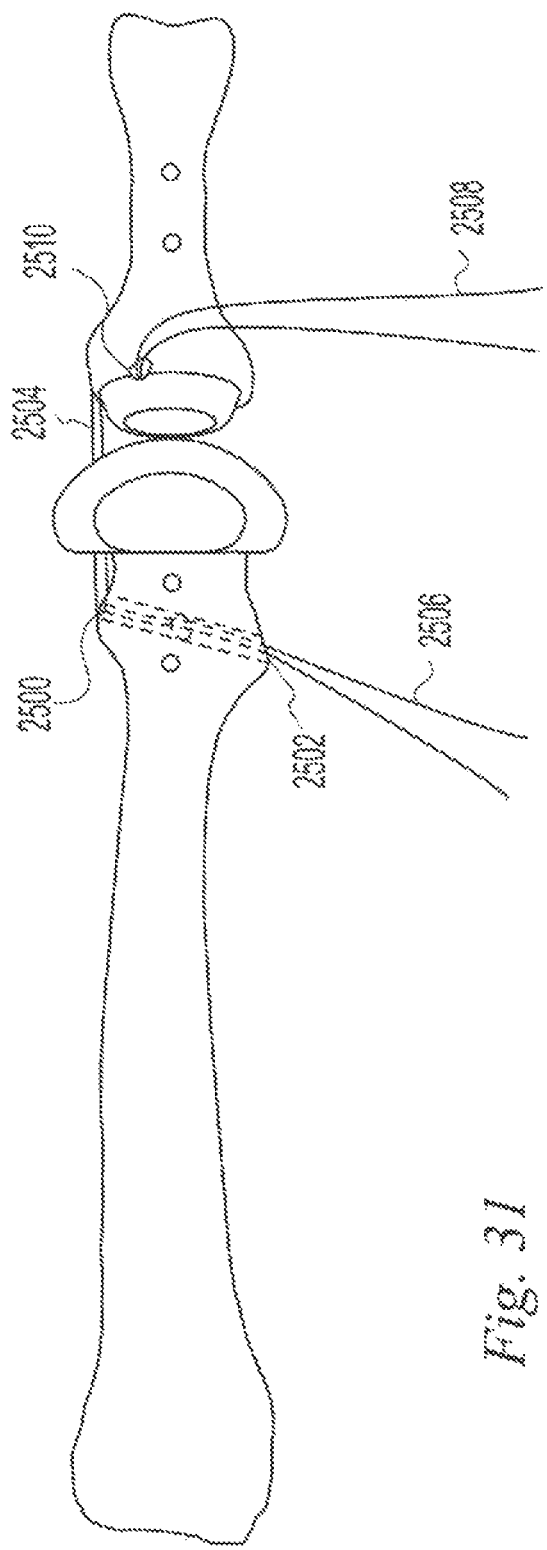

In FIG. 31 the sutures 2506, 2508 have been tensioned to pull the ends of the graft 2504 into the tunnels. The suture may be secured by any suitable method such as tying, securing over a button, securing with an interference fastener, or other suitable method. Similarly, the graft 2504 may be secured directly such as by interference fastener, pinning, or other suitable method.

Figure 32:
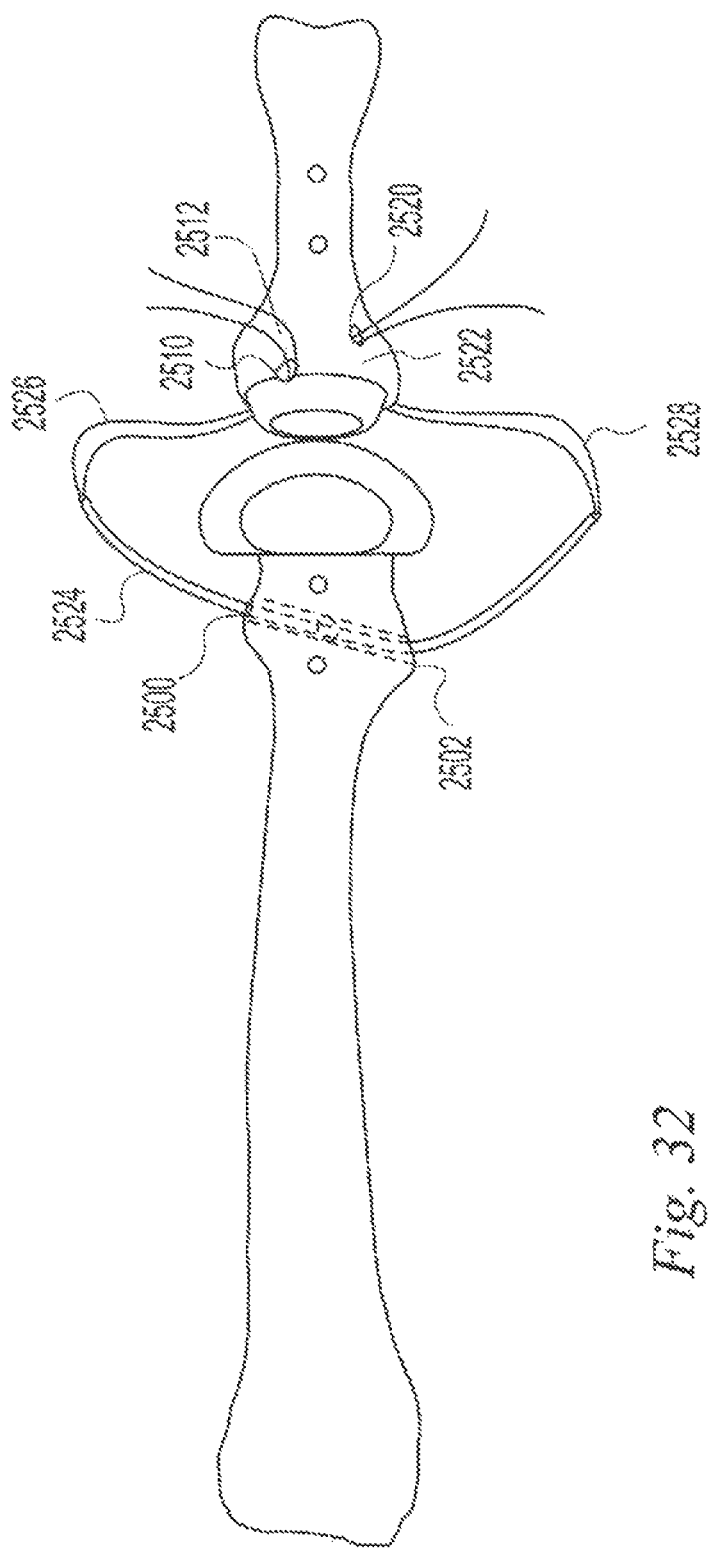
Figure 33:
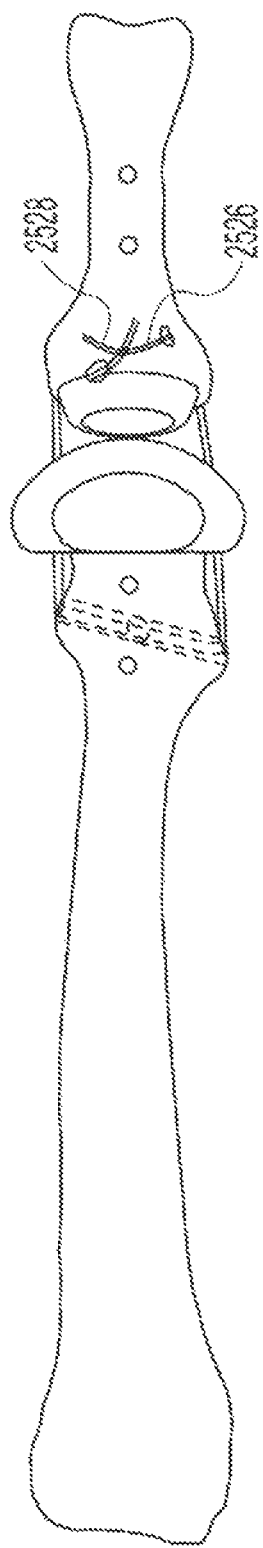
Figure 38:
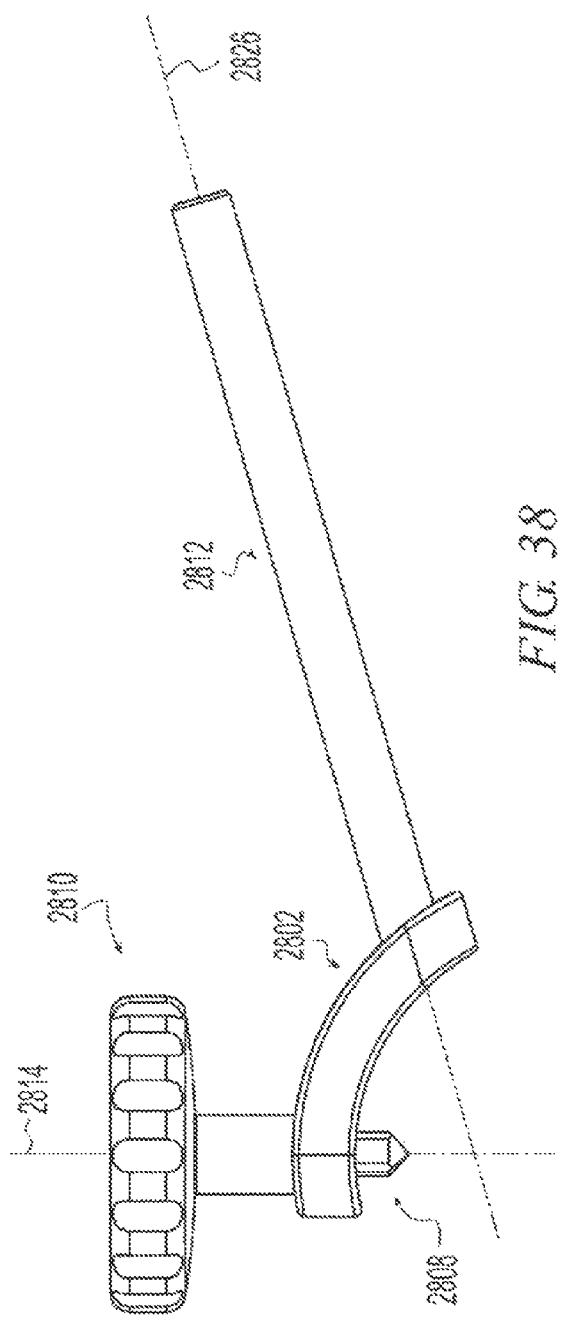
FIG. 38 is a side elevation view of the guide of FIG. 36.
Figure 39:
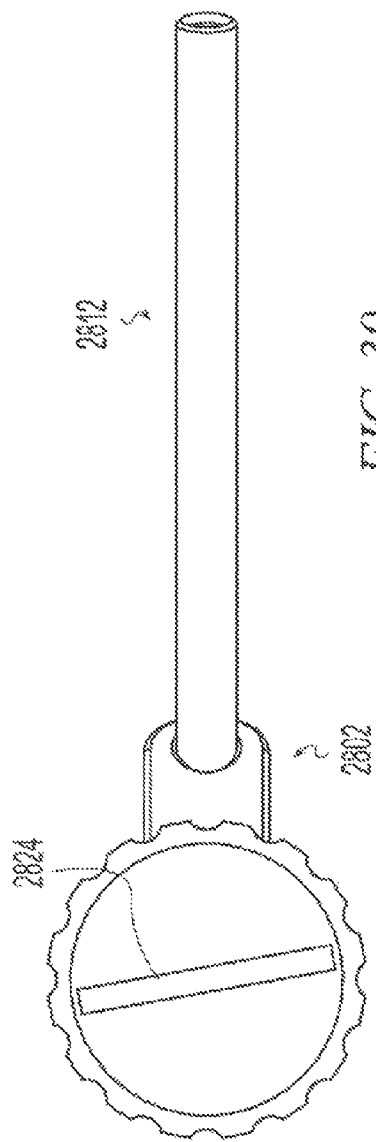
FIG. 39 is a top plan view of the guide of FIG. 36 taken along line 39-39 of FIG. 38.

FIGS. 32 and 33 depict an illustrative method to reconstruct a PCL. In the illustrative example of FIGS. 32 and 33, a bilateral reconstruction is shown in which both the medial and lateral PCLs are reconstructed. For example, the metatarsal guide portion 2312 of guide 2300 has guided a cutter to form a medial-dorsal tunnel 2500 extending from the medial PCL origin into the metatarsus and a lateral-dorsal tunnel 2502 extending from the lateral PCL origin into the metatarsus. The tubular extension 2314, 2315 of the metatarsal guide portion 2312 are oriented so that their axes intersect below the dorsal surface of the metatarsus. Thus, the tunnels 2500, 2502 intersect within the metatarsus and provide a path for fixing grafts to reconstruct one or both of the PCLs. The phalangeal guide portion 2344 has guided a cutter to form a tunnel 2510 extending from the medial-dorsal surface 2512 of the phalanx to the insertion 2514 of the lateral PCL on the lateral-plantar surface of the phalanx. The guide has also guided a cutter to form a tunnel 2520 extending from the lateral-dorsal surface 2522 of the phalanx to the insertion of the medial PCL on the medial-plantar surface of the phalanx. These two phalangeal tunnels cross each other without intersecting. A graft 2524 with a medial suture 2526 stitched to one end and a lateral suture 2528 stitched to another end. One of the sutures 2526, 2528 is threaded through the metatarsal bone tunnels and tensioned to pull the graft 2524 into the metatarsal bone tunnels. The medial suture 2526 is threaded through the phalangeal tunnel 2520 intersecting the medial PCL insertion by inserting it into the medial-plantar opening of the tunnel 2520 and retrieving it through the lateral-dorsal opening of the tunnel 2520. The lateral suture 2528 is threaded through the phalangeal tunnel 2510 intersecting the lateral PCL insertion by inserting it into the lateral-plantar opening of the tunnel 2510 and retrieving it through the medial-dorsal opening of the tunnel 2510.

In FIG. 33 the sutures 2526, 2528 have been tensioned to pull the graft ends into the phalangeal tunnels. The sutures may be secured by any suitable method such as tying, securing over a button, securing with an interference fastener, or other suitable method. Similarly, the graft may be secured directly such as by interference fastener, pinning, or other suitable method. In the illustrative example of FIGS. 32 and 33, the sutures have been secured by tying them together over the bone bridge between the tunnels 2510, 2520.

The medial and lateral ACLs of the MTP joint have origins that are coincident with the PCLs and insert into the junction between the edges of the plantar plate 44 and the intermetatarsal ligament (IML) 2700 at the medial and lateral borders of the plantar plate. The IML is a narrow band of connective tissue that extends between and connects together the heads of the metatarsal bones. The same tunnels used to reconstruct the PCLs may be used to reconstruct the ACLs such that the illustrative guides 2300, 2600 configured for PCL reconstruction may also be used for ACL reconstruction. FIGS. 34 and 35 depict an illustrative method to perform a bilateral ACL reconstruction. The method begins as in the bilateral PCL reconstruction with the formation of bone tunnels 2500, 2502 in the metatarsus and bone tunnels 2510, 2520 in the proximal phalanx. A graft 2702 is pulled through the metatarsal tunnels. The ends of the graft 2702 are passed through the IML 2700 at the anatomic insertion of the ACL and then into the phalangeal tunnels 2510, 2520 and secured. In the illustrative example of FIGS. 34 and 35 the graft is secured by tying sutures connected to the graft ends together over the bone bridge between the tunnels 2510, 2520. One or both ACLs may be reconstructed along with one or both PCLs. For example, a PCL graft 2504 may be attached as described relative to FIGS. 27-33 along with the ACL graft 2702.

The guides 2300, 2600 may have any number of cutter guides targeted at any desired anatomical feature. While the illustrative examples have depicted a guide configured for ACL and PCL reconstruction of the right human MTP joint, the guide may be similarly configured to target other ligament reconstructions or other surgical procedures at other locations throughout the body.

FIGS. 36-39 depict an illustrative example of a guide 2800 for guiding a cutter to cut a bone. In this illustrative example, the guide 2800 is configured as a drill guide to guide a drill, punch, pin, broach or the like to form holes in the bones adjacent the second MTP joint of the right human foot. The guide includes a base member 2802. In the illustrative examples of FIGS. 36-39, the base member 2802 is an arcuate member extending from a first end 2804 to a second end 2806. An indexing member 2808 and a grip 2810 are attached to the base member 2802 near the first end 2804. A guide member 2812 having a feature for guiding a tunnel forming implement is attached to the base member 2802 near the second end.

In the illustrative example of FIGS. 36-39, the indexing member 2808 and grip 2810 are coaxial relative to a first longitudinal indexing axis 2814. The indexing member 2808 is in the form of a sharply pointed four sided pyramid projecting inwardly on the concave side of the arcuate base member 2802. The grip 2810 includes a riser post 2816 extending upwardly from the convex side of the base member 2802 and is topped with a cylindrical thumb pad 2818 having a knurled perimeter 2820, an upwardly directed face having a central depression 2822 for receiving a user's thumb, and an alignment feature such for example an alignment mark 2824 inscribed on the face. The illustrative guide member 2812 is a tube having an interior bore for guiding a tunnel forming implement and defining a bore axis 2826. The indexing axis 2814 and bore axis 2826 form an angle between them of approximately 73 degrees and converge on the convex side of the base member. The indexing axis 2814, bore axis 2826, and alignment mark 2814 are oriented relative to one another based on averaged anthropometric data relating the dorsal surface of the metatarsus, the metatarsal longitudinal axis, and the metatarsal epicondyles.

As shown in FIGS. 41 and 40, with the indexing member engaged with the dorsal cortex of the metatarsal bone, the indexing axis perpendicular to the metatarsal axis, the alignment mark parallel to the metatarsal axis, and the bore axis directed toward the medial epicondyle, the bore axis 2814 will project through the metatarsal bone and intersect the medial and lateral epicondyles 32, 34. These references may be adjusted so that the bore axis 2814 projects slightly dorsal of the medial epicondyle and slightly plantar of the lateral epicondyle in order to provide additional clearance above the metatarsal bone medially for insertion of a cutter such as a drill. When a bone tunnel 2828 is formed along the bore axis, the tunnel exits will approximate the origins of the medial and lateral PCLs and ACLs at the epicondyles 32, 34. FIG. 41 illustrates the lateral opening of a tunnel 2828 formed using the guide 2800.

Figure 42:
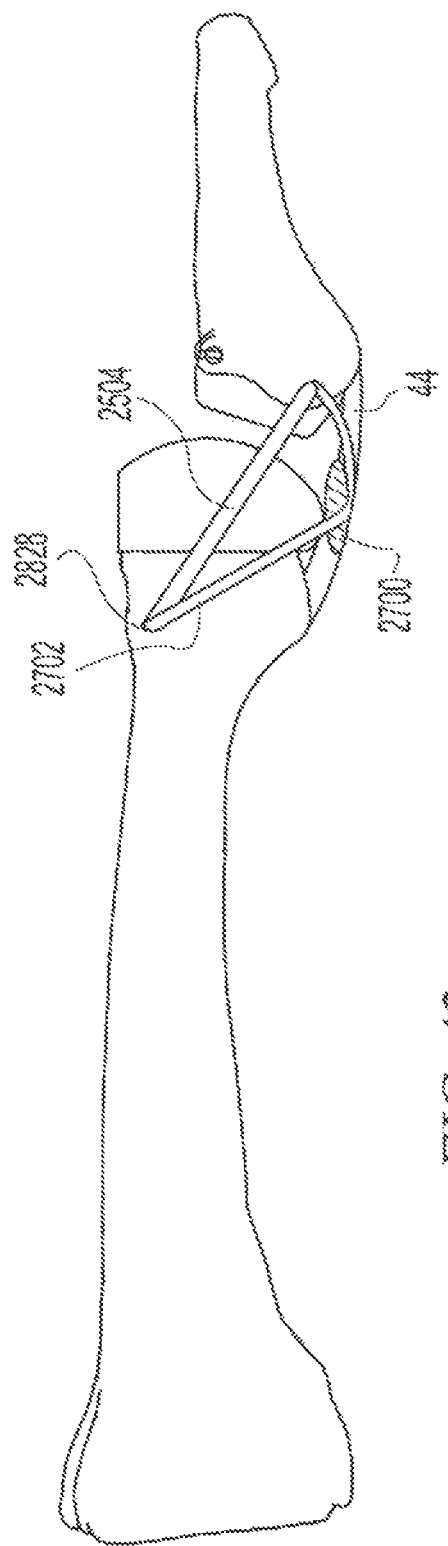
FIG. 42 illustrates soft tissue reconstruction of the MTP joint of the human foot using tunnels formed with a guide according to the present invention.

FIG. 42 illustrates reconstruction of the PCL and ACL similar to that of FIGS. 27-35 but utilizing a tunnel through the metatarsal epicondyles formed using the guide 2800. For a unilateral repair, the tunnel may go part way or all the way through the metatarsal bone and the graft may be secured using techniques such as tying, using interference devices, or other suitable methods. The tunnel 2828 may be used for PCL reconstruction, ACL reconstruction, and combined PCL and ACL reconstruction with the grafts 2504, 2704 routed as described relative to FIGS. 27-35.

Figure 43:
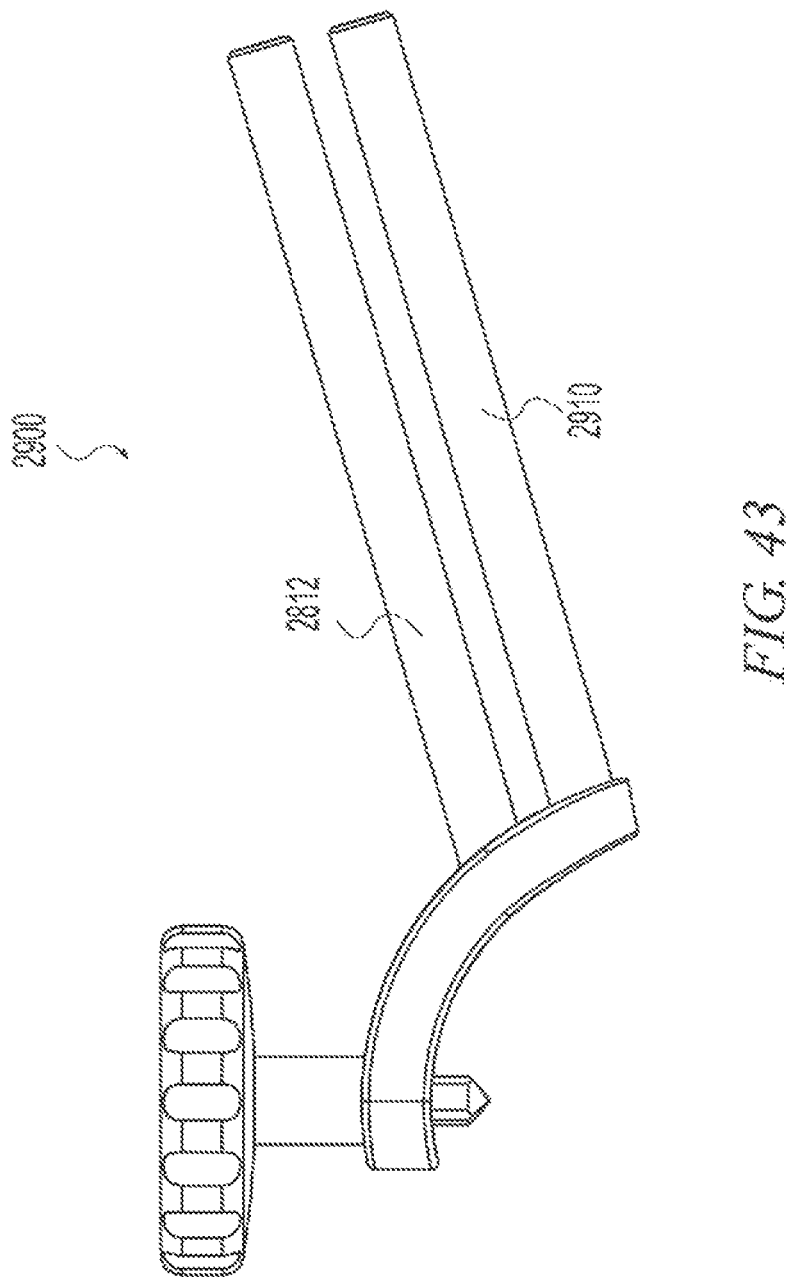
FIG. 43 is a side elevation view of an illustrative example of a guide according to the present invention.

FIG. 43 illustrates a guide 2900 similar to the guide 2800 of FIG. 36 but having a second guide member 2910 offset further plantar than a first guide member 2812. The guide member 2910 is oriented to produce a bone tunnel plantar the bone tunnel 2828 and useable to provide a tunnel for ACL reconstruction distinct from the tunnel for PCL reconstruction. The lower tunnel may be useful where, for example, the PCL's are intact and it is desirable to provide a tunnel for ACL reconstruction that does not compromise the PCL origins. It may also be used, for example, to provide separate tunnels for PCL and ACL reconstruction. The more plantar second guide member 2910 may be provided alone on a guide with the more dorsal first guide member 2812 omitted or they may both be placed on the same guide as shown.

Figure 44:
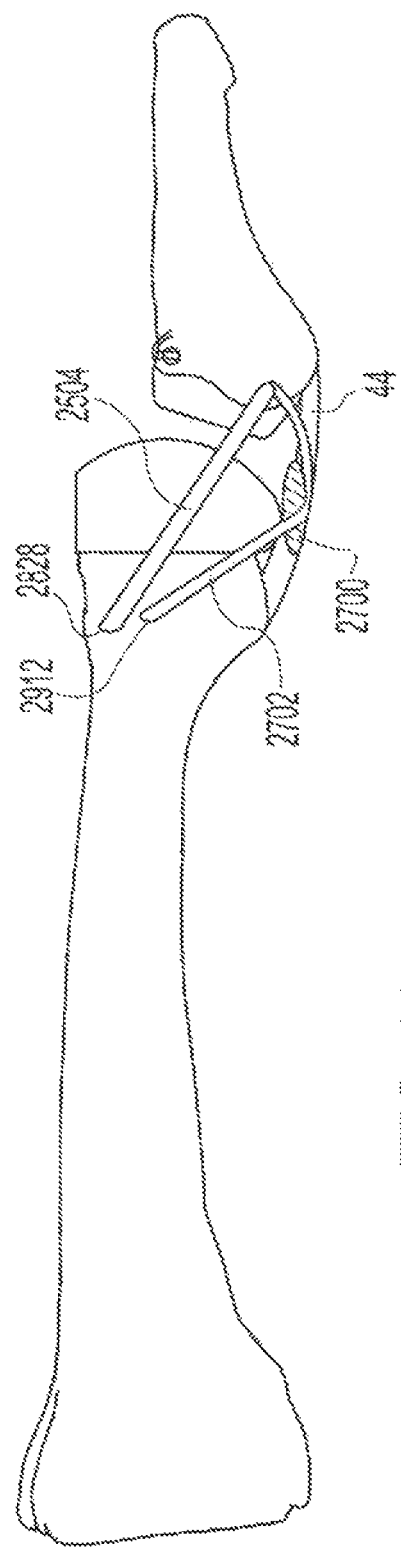
FIG. 44 illustrates soft tissue reconstruction of the MTP joint of the human foot using tunnels formed with a guide according to the present invention.

FIG. 44 illustrates two medial to lateral tunnels 2828, 2912 formed using the guide 2900 of FIG. 43 and separate reconstructions of the lateral PCL and lateral ACL with grafts 2504, 2702. The reconstructions shown in FIGS. 42 and 44 are hybrid constructs providing a combined PCL & ACL functional replacement utilizing a tunnel on the proximal phalanx for the attachment of both grafts.

Figure 45:
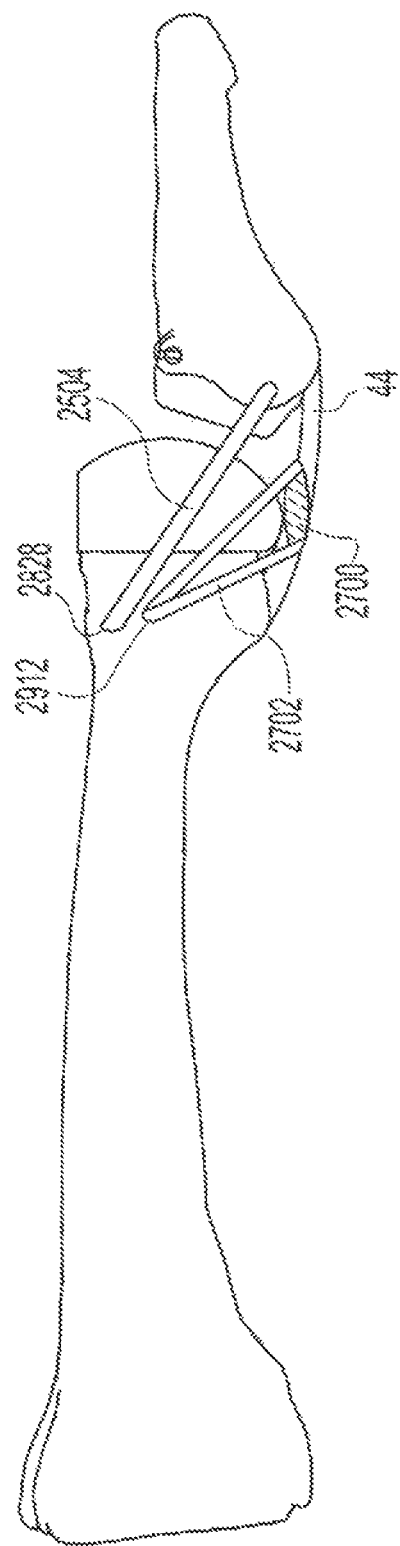
FIG. 45 illustrates soft tissue reconstruction of the MTP joint of the human foot using tunnels formed with a guide according to the present invention.

FIG. 45 illustrates an anatomic reconstruction of the PCL and an anatomic reconstruction of the ACL. The intact ACL is a fan shaped ligament that originates at the epicondyle on the metatarsal head and inserts into the border of the plantar plate. The medial ACL inserts into the medial border of the plantar plate and the lateral ACL inserts into the lateral border of the plantar plate. In the illustrative reconstruction of FIG. 45, the tunnel 2912 is located approximately at the origin of the ACL and a graft 2702 is passed from the tunnel 2912, under the intermetatarsal ligament 2700, and back to the tunnel 2912 where both ends of the graft 2702 are fixed to form a triangular graft construct similar to the intact ACL anatomy. In a bilateral ACL reconstruction, separate medial and lateral grafts may be passed and fixed in the tunnel 2912 or a single graft may be passed through the tunnel and on each side of the metatarsal head with ends brought back to the tunnel 2912 and fixed. The graft 2701 may pass around any portion of the intermetatarsal ligament 2700. For example, it may pass completely around the intermetatarsal ligament such that the portion includes the entire intermetatarsal ligament or it may pass through the metatarsal ligament and around a portion less than the entire ligament. The graft may pass through or around a portion of the plantar plate alone or in combination with the intermetatarsal ligament.

The surgical procedures and reconstructions relating to the MTP joint and surrounding bones may also be performed on corresponding joints and bones of the hand and such use is within the scope of the invention.

What is claimed is:

1. A bone drill guide useable near a metatarsal phalangeal (MTP) joint of a human foot to guide the formation of a hole in a bone that intersects a ligament boney attachment adjacent the joint, the MTP joint including a metatarsal bone having a longitudinal axis and a head with an articular surface, and a phalangeal bone having a head with an articular surface, the bone drill guide comprising:

a body having a reference member comprising a first reference portion, a second reference portion, and a first drill guiding portion, the first and second reference portions positioned on opposing sides of the reference member, the first reference portion engageable with at least one articular surface of the MTP joint and with the second reference portion engageable with at least one other articular surface of the MTP joint, the first drill guiding portion being oriented relative to the first reference portion based on human anatomy relating the location of a first ligament boney attachment to at least one articular surface of the MTP joint, the guide being operable to engage the first reference portion with at least one articular surface of the MTP joint to position the first drill guiding portion in alignment with the boney attachment of the first ligament.

2. The bone drill guide of claim 1 further comprising a second drill guiding portion, the second drill guiding portion being oriented relative to the first and second reference portions to align with a second ligament boney attachment simultaneous with the alignment of the first drill guiding portion with the first ligament boney attachment.

3. The bone drill guide of claim 1 wherein the bone drill guide is operable to engage the first reference portion with an anatomic landmark to position the first drill guiding portion in alignment with the first ligament boney attachment when the landmark is spaced away from the first ligament boney attachment.

4. A bone drill guide useable near a metatarsal phalangeal (MTP) joint of a human foot to guide the formation of a hole in a bone that intersects a ligament boney attachment adjacent the joint, the MTP joint including a metatarsal bone having a longitudinal axis and a head with an articular surface, and a phalangeal bone having a head with an articular surface, the bone drill guide comprising:
a body having a first reference portion engageable with at least one articular surface of the MTP joint and a first drill guiding portion, the first drill guiding portion being oriented relative to the first reference portion based on human anatomy relating the location of a first ligament boney attachment to at least one articular surface of the MTP joint, the guide being operable to engage the first reference portion with at least one articular surface of the MTP joint to position the first drill guiding portion in alignment with the boney attachment of the first ligament, and wherein the first reference portion comprises a member extending away from the body and having a concave surface engageable with the metatarsal head.

5. The bone drill guide of claim 4 wherein the concave surface is spherical and engageable with the metatarsal head, the spherical engagement operable to constrain the guide in three translational degrees of freedom.

6. The bone drill guide of claim 5 wherein the body comprises a guide longitudinal axis and a planar portion, the guide being operable, while the concave surface is engaged with the metatarsal head, to align the guide longitudinal axis parallel to the longitudinal axis of the metatarsal bone to eliminate two degrees of rotational freedom and to align the planar portion parallel to the transverse plane of the foot to eliminate a third degree of rotational freedom.

7. The bone drill guide of claim 4 wherein the concave surface is cylindrical and engageable with the metatarsal head, the cylindrical engagement operable to constrain the guide in two translational degrees of freedom.

8. The bone drill guide of claim 7 wherein the body comprises a guide longitudinal axis and a planar portion, the guide being operable, while the concave surface is engaged with the metatarsal head, to align the guide longitudinal axis with the longitudinal axis of the metatarsal bone to eliminate one degree of translational freedom and two degrees of rotational freedom and to align the planar portion parallel to the transverse plane of the foot to eliminate a third degree of rotational freedom.

9. A bone drill guide useable near a metatarsal phalangeal (MTP) joint of a human foot to guide the formation of a hole in a bone that intersects a ligament boney attachment adjacent the joint, the MTP joint including a metatarsal bone having a longitudinal axis and a head with an articular surface, and a phalangeal bone having a head with an articular surface, the bone drill guide comprising:
a body having a first reference portion engageable with at least one articular surface of the MTP joint and a first drill guiding portion, the first drill guiding portion being oriented relative to the first reference portion based on human anatomy relating the location of a first ligament boney attachment to at least one articular surface of the MTP joint, the guide being operable to engage the first reference portion with at least one articular surface of the MTP joint to position the first drill guiding portion in alignment with the boney attachment of the first ligament, and wherein the body comprises first and second rigid members joined together at a hinge in relative rotating relationship and the first drill guiding portion includes a hole defining a first drill guiding axis through the first rigid member alignable with the boney attachment of a ligament to the metatarsal bone.

10. The bone drill guide of claim 9 wherein the second rigid member includes a second drill guiding portion having a hole defining a second drill guiding axis simultaneously alignable with the boney attachment of a ligament to the phalangeal bone.

11. The bone drill guide of claim 10 wherein the first and second rigid members further include holes for receiving fixation members to attach the rigid members to the metatarsal and phalangeal bones.

12. A method of forming a tunnel in a bone near a bone joint to intersect a ligament boney attachment adjacent the bone joint, the method comprising:
positioning a guide adjacent the bone joint, the guide having a body comprising:
a reference member having a first reference portion and a second reference portion, the first reference portion engageable with at least a first articular surface of the bone joint, the second reference portion engageable with at least a second articular surface of the bone joint; and
a first guiding portion oriented relative to the first reference portion based on human anatomy relating anatomic landmarks associated with the kinematic operation of the bone joint to a ligament boney attachment;
engaging the first reference portion with the first articular surface and engaging the second reference portion with the second articular surface to position the first guiding portion in alignment with the ligament boney attachment; and
guiding a cutter with the first guiding portion to form a bone tunnel intersecting the ligament boney attachment.

13. The method of claim 12 wherein the first guiding portion is oriented relative to the second reference portion based on the human anatomy relating anatomic landmarks, and wherein the engaging includes the second reference portion engaging the second articular surface simultaneously with the first reference portion engaging the first articular surface.

14. The method of claim 12 wherein the first guiding portion comprises a drill guide, and wherein the cutter comprises a drill positioned within and guided along the drill guide.

15. The method of claim 12 wherein the bone joint is a metatarsal phalangeal (MTP) joint of a human foot, and wherein the first articular surface is positioned at a metatarsal head of a metatarsal bone of the human foot.

16. A method of forming a tunnel in a bone near a bone joint to intersect a ligament boney attachment adjacent the bone joint, the method comprising:
   positioning a guide adjacent the bone joint, the guide having a body comprising:
      a first reference portion engageable with the bone joint; and
      a first guiding portion oriented relative to the first reference portion based on human anatomy relating anatomic landmarks associated with the kinematic operation of the bone joint to a ligament boney attachment;
   engaging the first reference portion with a first anatomic landmark to position the first guiding portion in alignment with the ligament boney attachment; and
   guiding a cutter with the first guiding portion to form a bone tunnel intersecting the ligament boney attachment; and
   wherein the bone joint is a metatarsal phalangeal (MTP) joint of a human foot, wherein the first anatomic landmark comprises a metatarsal head of a metatarsal bone of the human foot, and wherein the first reference portion comprises a member extending outwardly from the body and having a concave surface, and wherein the engaging the first reference portion comprises engaging the concave surface with the metatarsal head.

17. The method of claim 16 wherein the concave surface is spherical, and wherein engaging the concave surface with the metatarsal head constrains the guide in three translational degrees of freedom.

18. The method of claim 17 wherein the body further comprises a guide longitudinal axis and a planar portion, the method further comprising:
   aligning the guide longitudinal axis parallel with a longitudinal axis of the metatarsal bone to eliminate two degrees of rotational freedom; and
   aligning the planar portion parallel with a transverse plane of the human foot to eliminate a third degree of rotational freedom.

19. The method of claim 16 wherein the concave surface is cylindrical, and wherein engaging the concave surface with the metatarsal head constrains the guide in two translational degrees of freedom.

20. The method of claim 19 wherein the body further comprises a guide longitudinal axis and a planar portion, the method further comprising:
   aligning the guide longitudinal axis with a longitudinal axis of the metatarsal bone to eliminate one degree of translational freedom and two degrees of rotational freedom; and
   aligning the planar portion parallel to a transverse plane of the human foot to eliminate a third degree of rotational freedom.

* * * * *